(12) United States Patent
Feldman et al.

(10) Patent No.: US 9,339,660 B2
(45) Date of Patent: May 17, 2016

(54) IMPLANTABLE MEDICAL DEVICE WITH ONE OR MORE MAGNETIC FIELD SENSORS TO ASSIST WITH EXTERNAL CHARGER ALIGNMENT

(71) Applicant: Boston Scientific Neuromodulation Corporation, Valencia, CA (US)

(72) Inventors: Emanuel Feldman, Simi Valley, CA (US); Jordi Parramon, Valencia, CA (US); Robert D. Ozawa, Woodland Hills, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 121 days.

(21) Appl. No.: 14/502,659

(22) Filed: Sep. 30, 2014

(65) Prior Publication Data
US 2015/0100109 A1    Apr. 9, 2015

Related U.S. Application Data

(60) Provisional application No. 61/887,237, filed on Oct. 4, 2013.

(51) Int. Cl.
*A61N 1/378* (2006.01)
*A61N 1/372* (2006.01)

(52) U.S. Cl.
CPC ........... *A61N 1/3787* (2013.01); *A61N 1/37223* (2013.01)

(58) Field of Classification Search
CPC ........... A61N 1/37223; A61N 1/37247; A61N 1/37252; A61N 1/37258; A61N 1/3787; H02J 5/005; H02J 7/0047; H02J 7/025

USPC ...................................................... 607/60, 61
See application file for complete search history.

(56) References Cited

U.S. PATENT DOCUMENTS

| | | | |
|---|---|---|---|
| 5,314,453 | A | 5/1994 | Jeutter |
| 5,749,909 | A | 5/1998 | Schroeppel et al. |
| 6,516,227 | B1 | 2/2003 | Meadows et al. |
| 6,553,263 | B1 | 4/2003 | Meadows et al. |
| 6,668,197 | B1 * | 12/2003 | Habib ............... A61B 5/0031 607/101 |
| 7,177,690 | B2 | 2/2007 | Woods et al. |
| 7,650,192 | B2 | 1/2010 | Wahlstrand |
| 7,774,069 | B2 | 8/2010 | Olson et al. |
| 7,948,208 | B2 | 5/2011 | Partovi et al. |

(Continued)

OTHER PUBLICATIONS

U.S. Appl. No. 61/877,877, filed Sep. 13, 2013, Funderburk.

*Primary Examiner* — Allen Porter, Jr.
(74) *Attorney, Agent, or Firm* — Lewis, Reese & Nesmith, PLLC

(57) ABSTRACT

An implantable medical device (IMD) is disclosed having one or more magnetic field sensors for measuring a strength of a magnetic charging field provided by an external charger and used to provide operational power to the IMD, for example, to charge its battery. The measured field strength data, or derivations of such data, are telemetered to the external charger, which further process the received data if necessary and can inform a user whether alignment between the external charger and IMD is sufficient, a misalignment direction, and/or a misalignment distance, so that the user can attempt to improve the alignment of the external charger. The one or more sensors are preferably placed at or equidistantly around a center axis of the IMD's charging coil. However, the sensors may be placed at any number of locations in the IPG, and at different distances from the center axis.

24 Claims, 16 Drawing Sheets

(56) References Cited

U.S. PATENT DOCUMENTS

| | | |
|---|---|---|
| 8,010,205 B2 | 8/2011 | Rahman et al. |
| 8,244,367 B2 | 8/2012 | Wahlstrand et al. |
| 8,285,363 B2 | 10/2012 | Malackowski et al. |
| 8,311,638 B2 | 11/2012 | Aghassian |
| 8,335,569 B2 | 12/2012 | Aghassian |
| 8,473,066 B2 | 6/2013 | Aghassian |
| 2003/0085684 A1* | 5/2003 | Tsukamoto .......... A61N 1/3787 320/108 |
| 2005/0165461 A1 | 7/2005 | Takeda et al. |
| 2007/0060980 A1 | 3/2007 | Strother et al. |
| 2008/0027293 A1* | 1/2008 | Vodermayer .......... A61M 1/127 600/300 |
| 2008/0027500 A1 | 1/2008 | Chen |
| 2009/0069869 A1 | 3/2009 | Stouffer et al. |
| 2009/0112291 A1 | 4/2009 | Wahlstrand et al. |
| 2009/0118796 A1 | 5/2009 | Chen et al. |
| 2009/0222066 A1 | 9/2009 | Chen et al. |
| 2009/0259273 A1* | 10/2009 | Figueiredo ............. A61N 1/378 607/32 |
| 2010/0201315 A1 | 8/2010 | Oshimi et al. |
| 2010/0204756 A1 | 8/2010 | Aghassian |
| 2011/0004278 A1 | 1/2011 | Aghassian et al. |
| 2011/0093048 A1 | 4/2011 | Aghassian |
| 2011/0196452 A1 | 8/2011 | Forsell |
| 2012/0277831 A1* | 11/2012 | Joshi .................. A61N 1/37223 607/62 |
| 2013/0023958 A1* | 1/2013 | Fell ...................... A61N 1/3787 607/61 |
| 2013/0123881 A1 | 5/2013 | Aghassian |
| 2015/0028798 A1* | 1/2015 | Dearden ............. A61N 1/36125 320/107 |

* cited by examiner

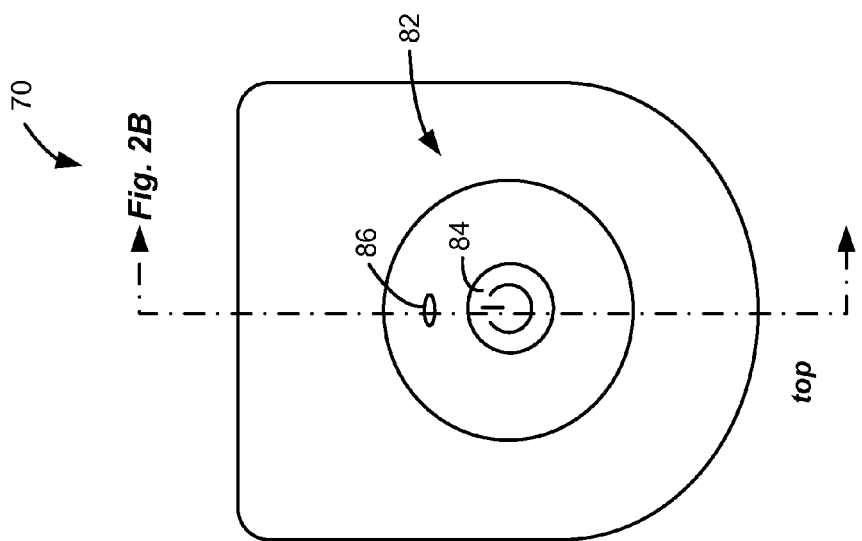
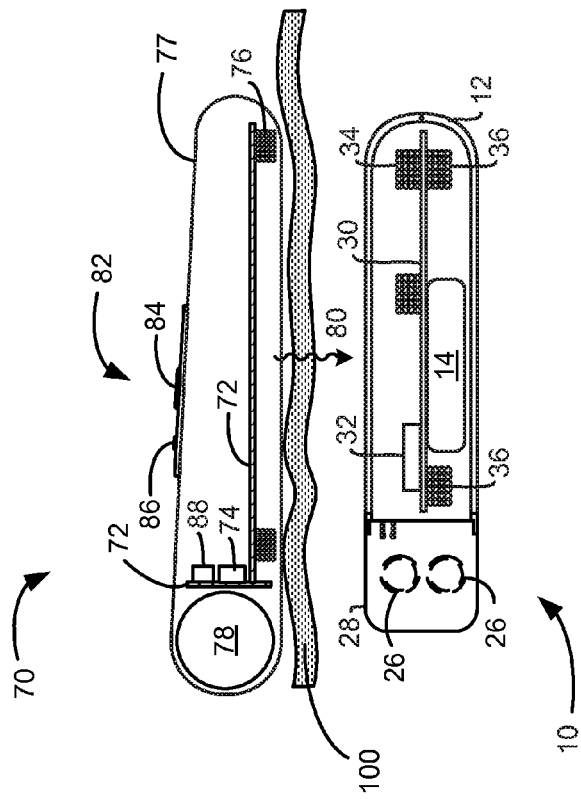
*Figure 2B (prior art)*
*Figure 2A (prior art)*

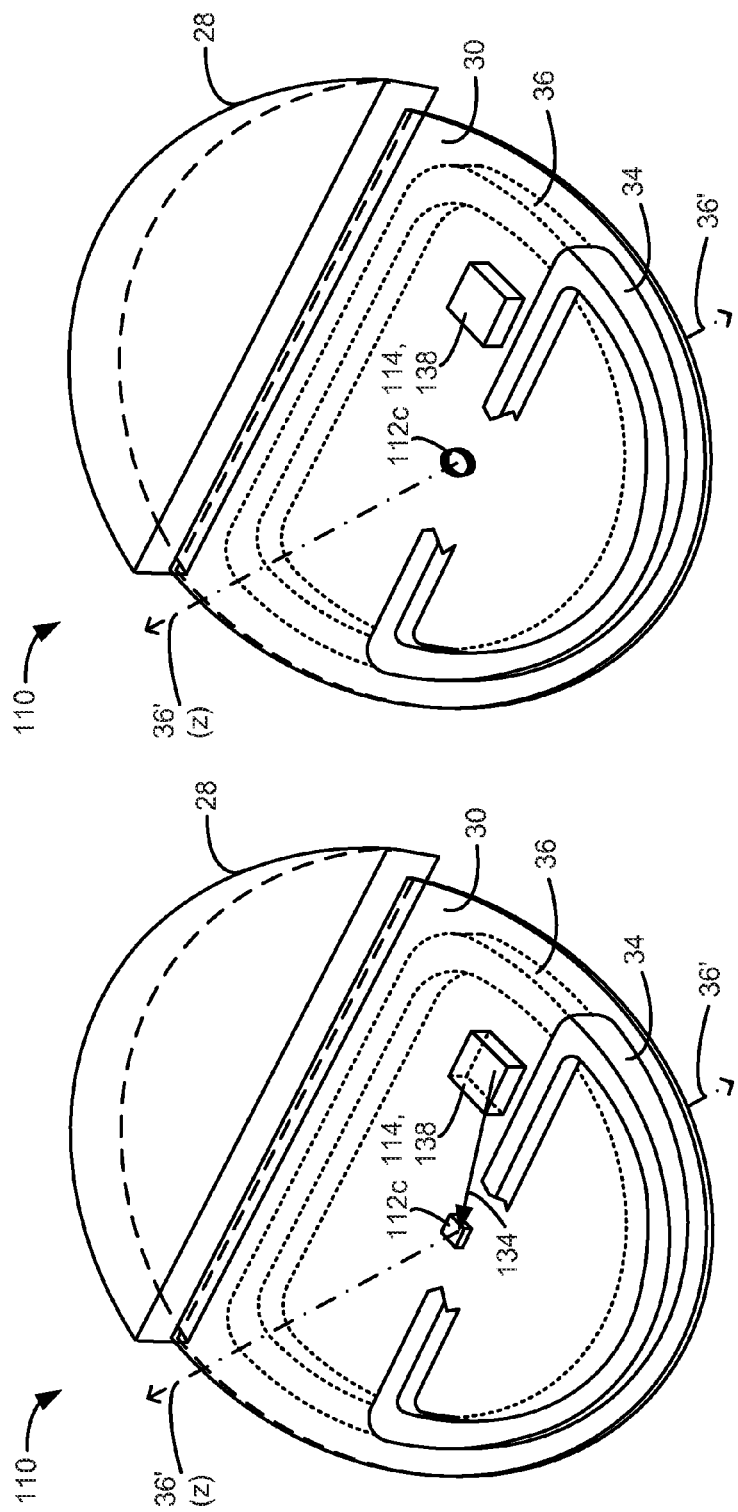

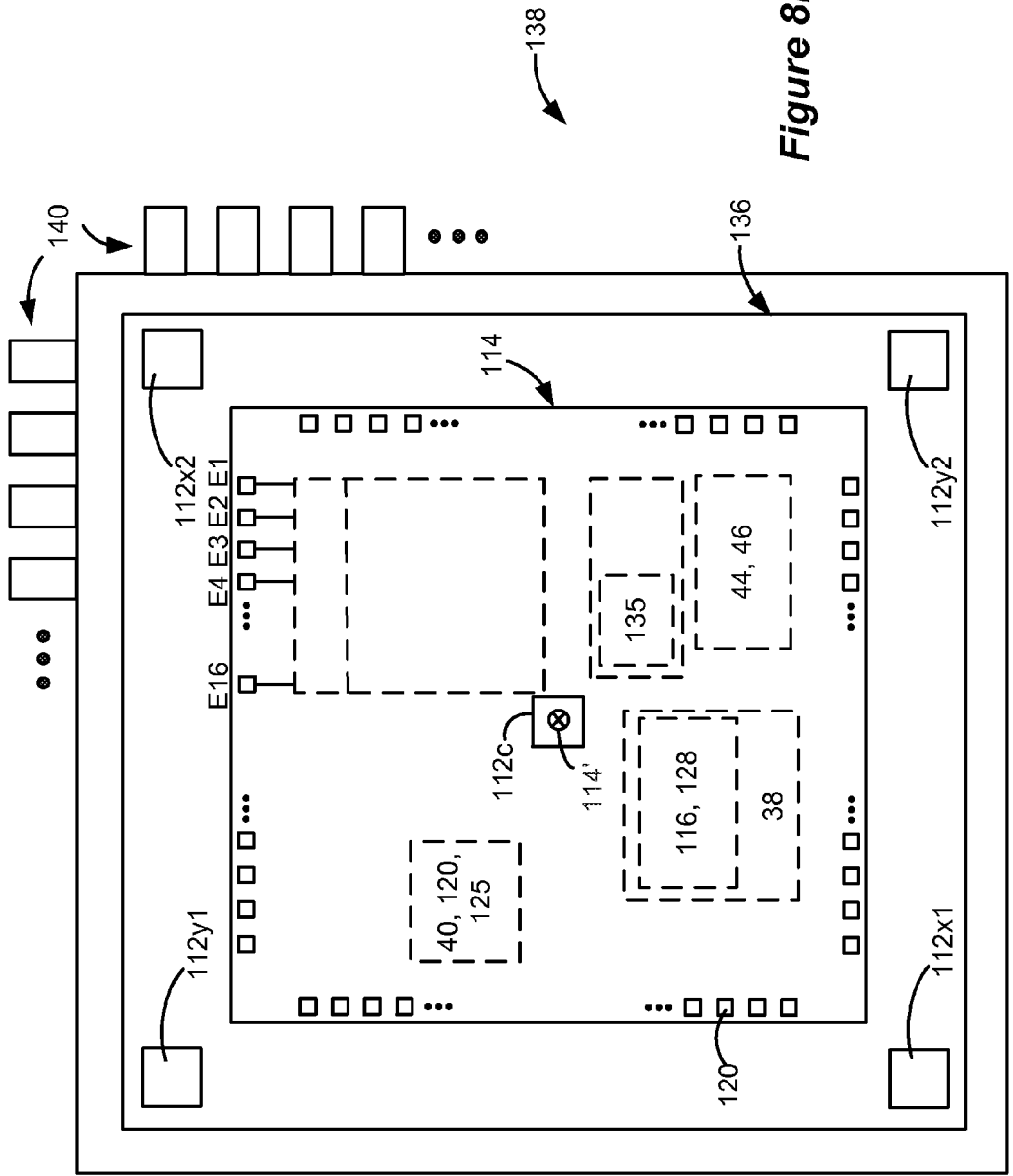

100 # IMPLANTABLE MEDICAL DEVICE WITH ONE OR MORE MAGNETIC FIELD SENSORS TO ASSIST WITH EXTERNAL CHARGER ALIGNMENT

CROSS REFERENCE TO RELATED APPLICATIONS

This is a non-provisional of U.S. Provisional Patent Application Ser. No. 61/887,237, filed Oct. 4, 2013, which is incorporated herein by reference, and to which priority is claimed.

FIELD OF THE INVENTION

The present invention relates to wireless communications with and wireless charging of an implantable medical device such as an implantable pulse generator.

BACKGROUND

Implantable stimulation devices are devices that generate and deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability in any implantable medical device system.

As shown in FIGS. 1A and 1B, a SCS system typically includes an Implantable Pulse Generator (IPG) 10, which includes a biocompatible device case 12 formed of metallic material such as titanium for example. The case 12 typically houses the circuitry and battery 14 (FIG. 2B) necessary for the IPG to function, although IPGs can also be powered via external RF energy and without a battery. The IPG 10 is coupled to electrodes 16 via one or more electrode leads (two such leads 18 are shown), such that the electrodes 16 form an electrode array 20. The electrodes 16 are carried on a flexible body 22, which also houses the individual signal wires 24 coupled to each electrode. In the illustrated embodiment, there are eight electrodes on each lead, although the number of leads and electrodes is application specific and therefore can vary. The leads 18 couple to the IPG 10 using lead connectors 26, which are fixed in a header 28 comprising epoxy for example, which header is affixed to the case 12. In a SCS application, distal ends of electrode leads 18 are typically implanted on the right and left side of the dura within the patient's spinal cord. The proximal ends of leads 18 are then tunneled through the patient's tissue 100 to a distant location such as the buttocks where the IPG 10 is implanted, where the proximal leads ends are then connected to the lead connectors 26.

As shown in cross section in FIG. 2B, the IPG 10 typically includes an electronic substrate assembly including a printed circuit board (PCB) 30 containing various electronic components 32 necessary for operation of the IPG 10, some of which are described subsequently. Two coils are generally present in the IPG 10: a telemetry coil 34 used to transmit/receive data to/from an external controller (not shown); and a charging coil 36 for charging or recharging the IPG's battery 14 using an external charger 70 (FIG. 2A). These coils 34 and 36 are also shown in the perspective view of FIG. 1B, which omits the IPG case 12 for easier viewing. Although shown as inside the case 12 in the Figures, the telemetry coil 34 can alternatively be fixed in header 28. Coils 34 and 36 may alternative be combined into a single telemetry/charging coil.

FIG. 2A shows a plan view of the external charger 70, and FIG. 2B shows it in cross section and in relation to the IPG 10 during a charging session. The external charger 70 is used to wirelessly provide operational power to the implantable medical device, such as to charge or recharge the IPG's battery 14, and includes at least one PCB 72 (two are shown; see U.S. Patent Application Publication 2008/0027500); electronic components 74, some of which are subsequently discussed; a charging coil 76; and a battery 78 for providing operational power for the external charger 70 and for the production of a magnetic charging field 80 from the coil 76. These components are typically housed within a case 77 which is sized to be hand held and portable, which may be made of plastic for example.

The external charger 70 has a user interface 82, which typically comprises an on/off switch 84 to activate the production of the magnetic charging field 80; an LED 86 to indicate the status of the on/off switch 84; and a speaker 88. The speaker 88 emits a "beep" for example if the external charger 70 detects that its charging coil 76 is not in good alignment with the charging coil 36 in the IPG 10 during a charging session, as discussed further below. The external charger 70 may be placed in a pouch around a patient's waist to position the external charger 70 in alignment with the IPG 10 during a charging session. Typically, the external charger 70 is touching the patient's tissue 100 during a charging session as shown, although the patient's clothing or the material of the pouch may intervene.

Wireless power transfer from the external charger 70 to the IPG 10 occurs by magnetic inductive coupling between coils 76 and 36. Referring to FIG. 3, when the external charger 70 is activated (e.g., on/off switch 84 is pressed), a charging circuit 94 under control of control circuitry 92 (e.g., a microcontroller) energizes coil 76 with a non-data-modulated AC current (Icharge) to create a magnetic charging field 80. The frequency of the magnetic charging field 80 may be on the order of 80 kHz for example, and may be set by the inductance of the coil 76 and the capacitance of a tuning capacitor (not shown). The magnetic charging field 80 induces a current in the IPG 10's charging coil 36, which charging circuitry in the IPG 10 uses to provide operational power to the IPG 10. For example, in an IPG with a rechargeable battery 14, charging circuitry can include a rectifier 44 to produce a DC voltage used to provide a charging current (Ibat) to recharge the IPG's battery 14, perhaps using an intermediate charge control and battery protection circuit 46 as shown. Wireless power transfer occurs transcutaneously through the patient's tissue 100.

The IPG 10 can also communicate data back to the external charger 70 along link 81 using Load Shift Keying (LSK) telemetry. Relevant data, such as the capacity of the battery, is sent from control circuitry 38 in the IPG 10 (e.g., a microcontroller) to a LSK modulator 40, which creates a series of digital data bits (LSK data 48). This data is input to the gate of a load transistor 42 to modulate the impedance of the charging coil 36 in the IPG 10. Such modulation of the charging coil 36 is detectable at the external charger 70 due to the mutual inductance between the coils 76 and 36, and will change the magnitude of the AC voltage needed at coil 76 (Vcoil) to drive the charging current, Icharge. If coil 36 is shorted (LSK data=1), Vcoil increases (Vcoil$_1$) to maintain Icharge; if not shorted (LSK data=0), Vcoil decreases (Vcoil$_0$), as shown in the waveform in FIG. 5. LSK demodulator 96 (receiver circuitry) in the external charger 70 can detect these changes in Vcoil (ΔV) to recover the series of digital data bits, which data is then received at control circuitry 92 so that appropriate action can be taken, such as ceasing production of the magnetic charging field 80 (i.e., setting Icharge to zero) when the battery 14 in the IPG 10 is fully charged. Note that the nature of LSK telemetry as described here only allows for telemetry from the IPG 10 to the external charger 70 when a magnetic charging field 80 is being produced, and requires the external charger 70 to be close the IPG 10. See, e.g., U.S. Patent Application Publication 2013/0123881 for further details regarding the use of LSK telemetry in an external charger system.

It is generally desirable to charge the IPG's battery 14 as quickly as possible to minimize inconvenience to the patient. One way to decrease charging time is to increase the strength of the magnetic charging field 80 by increasing Icharge in the charging coil 76 of the external charger 70. Increasing the magnetic charging field 80 will increase the current/voltage induced in the coil 36 of the IPG 10, which increases the battery charging current, Ibat, hence charging the battery 14 faster.

However, the strength of the magnetic charging field 80 can only be increased so far before heating becomes a concern. Heating is an inevitable side effect of inductive charging using magnetic fields, and can result because of activation of relevant charging circuitry in the external charger 70 or IPG 10, or as a result of eddy currents formed by the magnetic charging field 80 in conductive structures in either device. Heating is a safety concern. The external charger 70 is usually in contact with the patient's tissue 100 during a charging session, and of course the IPG 10 is inside the patient. If the temperature of either exceeds a given safe temperature, the patient's tissue may be aggravated or damaged.

The alignment between the external charger 70 and the IPG 10 can affect heating, as shown in FIGS. 4A and 4B. In FIG. 4A, the charging coils 76 and 36 in the external charger 70 and the IPG 10 are well aligned, because the axes 76' and 36' around which the coils 76 and 36 are wound are collinear. As such, these coils 76 and 36 are well coupled electrically, meaning that a higher percentage of the power expended at coil 76 in creating the magnetic charging field 80 is actually received at coil 36, which leads to higher values for Ibat. In FIG. 4B, the charging coils 76 and 36 are laterally (radially) misaligned (r), which reduces the electrical coupling between the coils. Increasing the vertical distance d between the coils 76 and 36 (FIG. 4C), or increasing the angle (A) between the preferably parallel planes in which they reside (FIG. 4D), will also reduce coupling.

If it is desired that the alignment scenarios of FIGS. 4A and 4B charge the battery 14 at the same rate (Ibat=Y), then a higher value for Icharge (Icharge>X) will be needed in the misaligned scenario of FIG. 6B compared to the well-aligned scenario of FIG. 4A (Icharge=X). A higher value for Icharge in FIG. 4B will create a more intense magnetic charging field 80 that tends to increase the temperature of the environment (T>Z) when compared to the temperature of the environment in FIG. 4A (T=Z). If it is desired that the temperature be the same for both scenarios, then Icharge can be lowered in FIG. 4B, but this will also lower Ibat, and hence the battery 14 in that scenario would take longer to charge. In short, misalignment between the external charger 70 and the IPG 10 is not desired.

Accordingly, the art has disclosed several manners for determining misalignment between an external charger and an IPG, which techniques usually result in some form of user-discernible output letting the patient know when alignment is poor (such as via speaker 88 discussed earlier). Such techniques may also inform a patient how to fix the alignment, such as by indicating a direction the external charger should be moved relative to the IPG 10. See, e.g., U.S. Pat. Nos. 8,473,066 and 8,311,638.

Previous external charger alignment techniques however are difficult to implement, and may not precisely determine alignment as they rely on inferences gleaned from electrical measurements taken at the external charger during the charging session. For example, one prior art alignment techniques relies on determining the loading of the charging coil in the external charger during production of the magnetic charging field. Specifically, the voltage across the charging coil (Vcoil) is reviewed at the external charger and compared to a Vcoil threshold to determine alignment. This technique though suffers in its inability to distinguish between the scenarios of FIGS. 4B and 4C for example. In either of these scenarios, Vcoil would be higher due to poor coupling, but in FIG. 4B the poor coupling arises from misalignment (r), whereas in FIG. 4C the alignment is as good as it can be given the IPG 10's depth (d). A modification to this technique helpful in distinguishing these scenarios requires transmitting the magnetic charging field at different frequencies and measuring the input current to the charging coil in the external charger to estimate an implant depth (d), and thus to set an appropriate Vcoil threshold. See, e.g., U.S. Patent Application Publication 2010/0137948. However, the additional overhead of having to produce magnetic charging fields at different frequencies makes this technique complicated.

Other alignment techniques require the external charger to have positioning coils in addition to the main charging coil (e.g., 76), which positioning coils are used to sense magnetic fields in the environment. In these techniques, measurements taken from the positioning coils during the charging session are used to determine misalignment, and to indicate a direction the external charger can be moved to improve alignment (coupling). See, e.g., U.S. Pat. Nos. 8,473,066 and 8,311,638. But these positioning-coil measurements again rely on loading, and therefore are indirect. Moreover, assessing the loading of the position coils does not necessarily discriminate between loading caused by coupling of the charging coil in the IPG, and coupling caused by other sources, such as the conductive material used for the IPG's case. Moreover, while positioning coils can provide a general sense of the misalignment direction between the external charger and the IPG, they do not compute a misalignment distance—i.e., how far the external charger must be moved in the misalignment direction to achieve good alignment. Such data would be useful to the user who is attempting to improve external charger alignment with her IPG. A more accurate means of determining external charger/IPG alignment is therefore desired.

BRIEF DESCRIPTION OF THE DRAWINGS

FIGS. 2A and 2B show an external charger for an IPG and the manner in which they communicate in accordance with the prior art.

FIGS. 5A and 5B show an improved IPG which includes at least one magnetic field sensor.

FIGS. 8A and 8B show incorporation of the one or more magnetic field sensors in an integrated circuit used in the improved IPG, or in the package of an integrated circuit used in the improved IPG.

DETAILED DESCRIPTION

An improved implantable medical device such as an Implantable Pulse Generator (IPG) is disclosed having one or more magnetic field sensors at one or more locations for measuring a strength of a magnetic charging field provided by an external charger and used to provide operational power to the IPG, for example, to charge the IPG's battery. Alignment data indicative of a strength of the magnetic charging field at the one or more locations and thus indicative of external charger alignment with respect to the IPG, are telemetered to the external charger, which can further process the received data if necessary. The external charger provides from its user interface alignment information based on the received alignment data, such as whether or not alignment between the external charger and IPG is sufficient, a misalignment direction, and/or a misalignment distance. Upon reviewing such information, the user can attempt to improve the alignment of the external charger to shorten the charging session and to render it less susceptible to heating. The one or more magnetic field sensors are preferably placed at or equidistantly around a center axis of the IPG's charging coil. However, the sensors may be placed at any number of locations in the IPG (on the IPG's PCB, integrated in an integrated circuit or integrated circuit package, in or on the IPG's case, etc.), and at different distances from the center axis. Sensor offset data indicative of the locations of the sensors in the IPG relative to the center axis can assist with processing or deriving the alignment data if necessary.

FIG. 5A shows an improved IPG 110 containing a magnetic field sensor 112. As shown with the conductive IPG case 12 removed for easier viewing, the magnetic field sensor 112c is preferably affixed to the PCB 30 in the IPG 110 at the center axis 36' of the IPG's charging coil 36 (hence denoted as "c"). Although shown on the top of the PCB 30, the magnetic field sensor 112c could also occur on the bottom of the PCB 30, or in other locations as discussed subsequently.

Figure 4A:
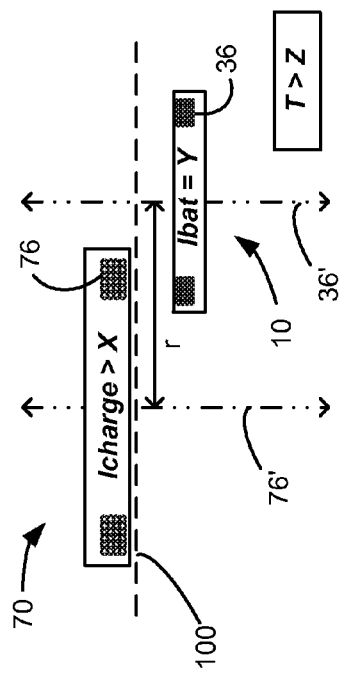
FIGS. 4A-4D show different alignment scenarios between the external charger and the IPG in accordance with the prior art.
Figure 4C:
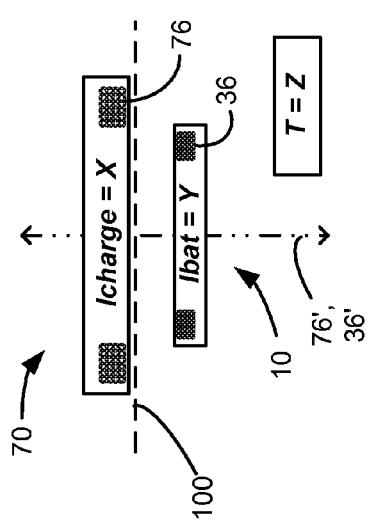
Figure 4B:
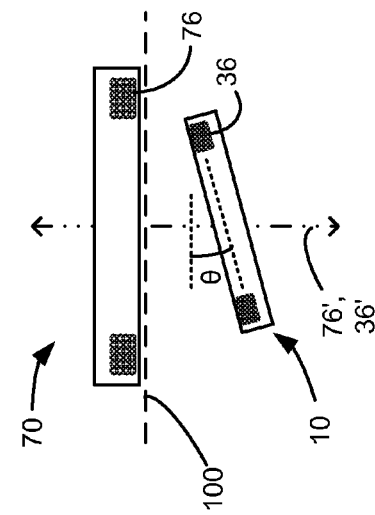
Figure 4D:
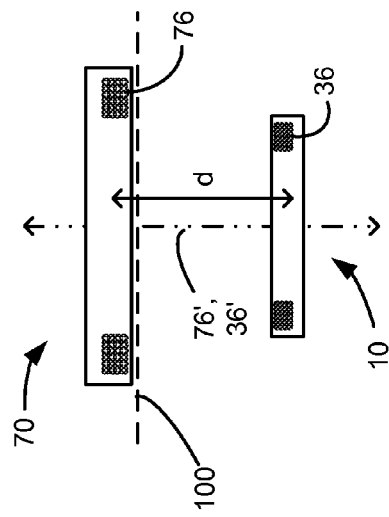
Figure 5C:
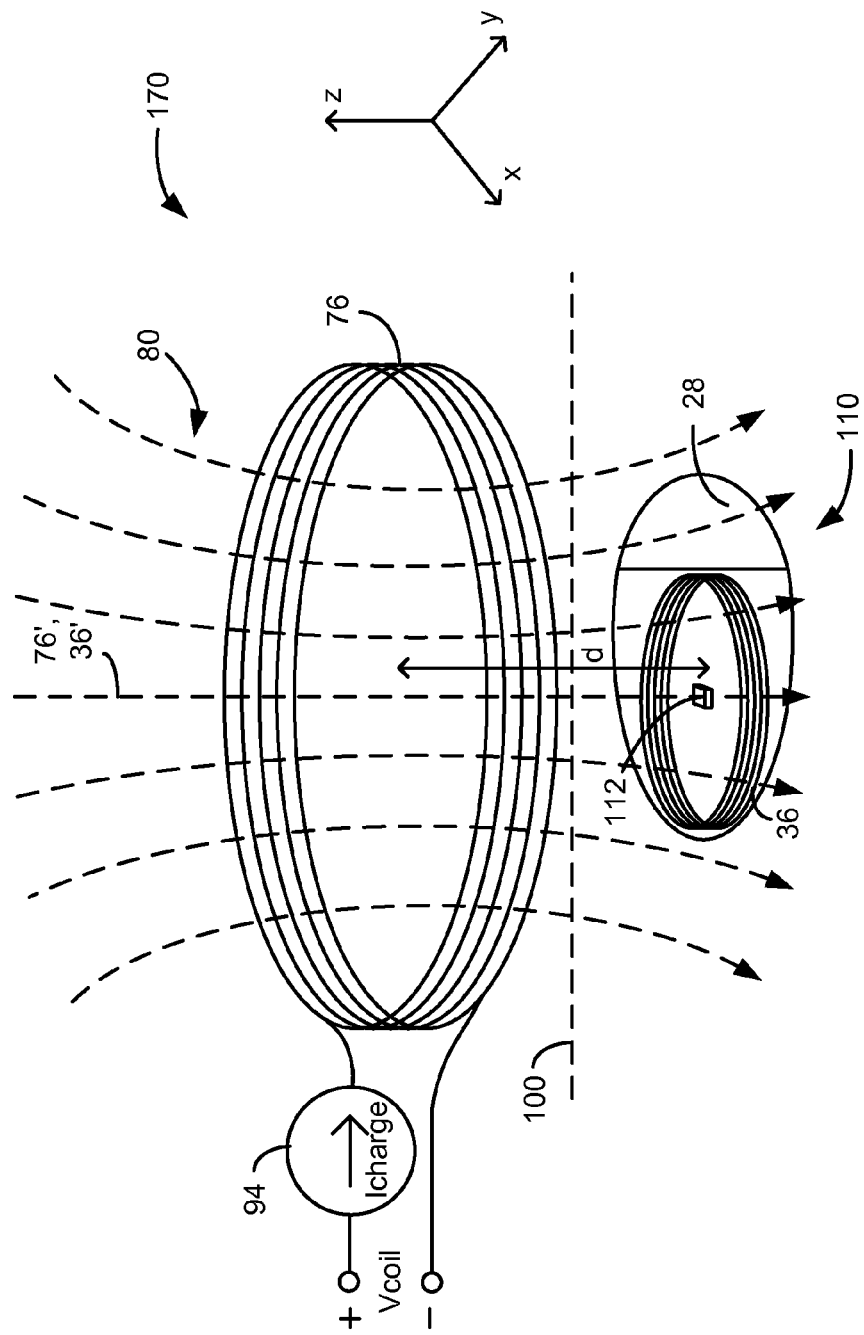
FIG. 5C shows the shape of a magnetic charging field and how the at least one magnetic field sensors measures a strength of the field.

Placement of the magnetic field sensor 112c at the center axis 36' assists in determining external charger/IPG alignment, as illustrated in FIG. 5C, which shows a simple schematic of an improved external charger 170 for use with the improved IPG 110. FIG. 5C shows the general shape of the magnetic charging field 80 produced by charging coil 76 during a charging session. As one skilled in the art will appreciate, the magnetic flux lines in the magnetic charging field 80 are densest along center axis 76' of the charging coil 76. Thus, the magnetic charging field 80 is strongest along this (z) axis 76' at a given IPG depth, d, and will decrease as one moves away (radially, in x or y) from the axis 76' at this depth (see FIG. 4B).

By placing the magnetic field sensor 112c at center axis 36' in the IPG 110, the IPG 110 can sense when axes 76' and 36' are collinear—and hence when external charger/IPG alignment and electrical coupling are ideal for the given depth—by sensing a maximum strength for the magnetic charging field 80. By contrast, if the external charger 170 is radially misaligned with the IPG 110, the axes 76' and 36' will not be collinear, and the magnetic field sensor 112c will sense a lesser strength of the magnetic field. By telemetering data relevant to the magnetic charging field 80 measured at the magnetic field sensor 112 from the IPG 110 to the external charger 170, the external charger 170 can provide alignment information to the user, as discussed further below.

While the above physics is easiest to understand with reference to coils 76 and 36 in the external charger 170 and IPG 110 that are perfectly circular and that thus have easily identified center axes 76' and 36', it should be noted that the disclosed technique can be used with coils that are not perfectly circular. For example, the charging coil 36 in the IPG 110 is not perfectly circular, as shown in FIG. 5A. Yet, one can still define an axis 36' that essentially denotes the center of the coil 36 where the magnetic field sensor 112c is ideally placed. Such center, and hence center axis 36', may for example pass through the centroid of the area inside the coil 36. Or the center axis 36' may be determined by experimentation as the location in the IPG 110 corresponding to axis 76' that gives rise to the highest coupling between the coils 76 and 36, for example, where the DC voltage produced by rectifier 44 (FIG. 5D) is highest, or where the battery charging current, Ibat, is highest. In any event, it is not strictly required that the magnetic field sensor 112c be placed at the exact center of the coil 36, as the disclosed alignment technique can still be used if the sensor 112c is close enough to this center. A center axis 76' for a non-circular charging coil 76 in the external charger 170 can be similarly determined.

The magnetic field sensor 112c can comprise any well-known device for detecting the strength of a magnetic field, including a Hall effect sensor, and a giant magnetoresistance (GMR) sensor. Sensor 112c can also comprise a pick-up coil, such as is shown in the example of FIG. 5B, which may comprise a traditional coil winding, or a winding formed in the conductive traces in the PCB 30. See, e.g., U.S. Patent Application Publication 2009/0222066. In any event, the magnetic field sensor 112c will output a signal, such as a voltage or current, proportional to the detected strength of the magnetic charging field 80. Such proportionality between the output voltage or current and the magnetic charging field strength need not be linear, and can be an inverse proportion depending on detection circuitry incorporated with the magnetic field sensor 112c. Direct linear proportionality in between detected magnetic field strength and output voltage, Vc, will be assumed here for simplicity.

In a preferred embodiment, the magnetic field sensor 112c is oriented to determine the strength of the magnetic charging field 80 along the z axis, i.e., in the direction parallel to axis 36'. However, one or more sensors 112 could also be used to detect the strength of the magnetic field 80 along other axes (e.g., x and y).

Figure 5D:
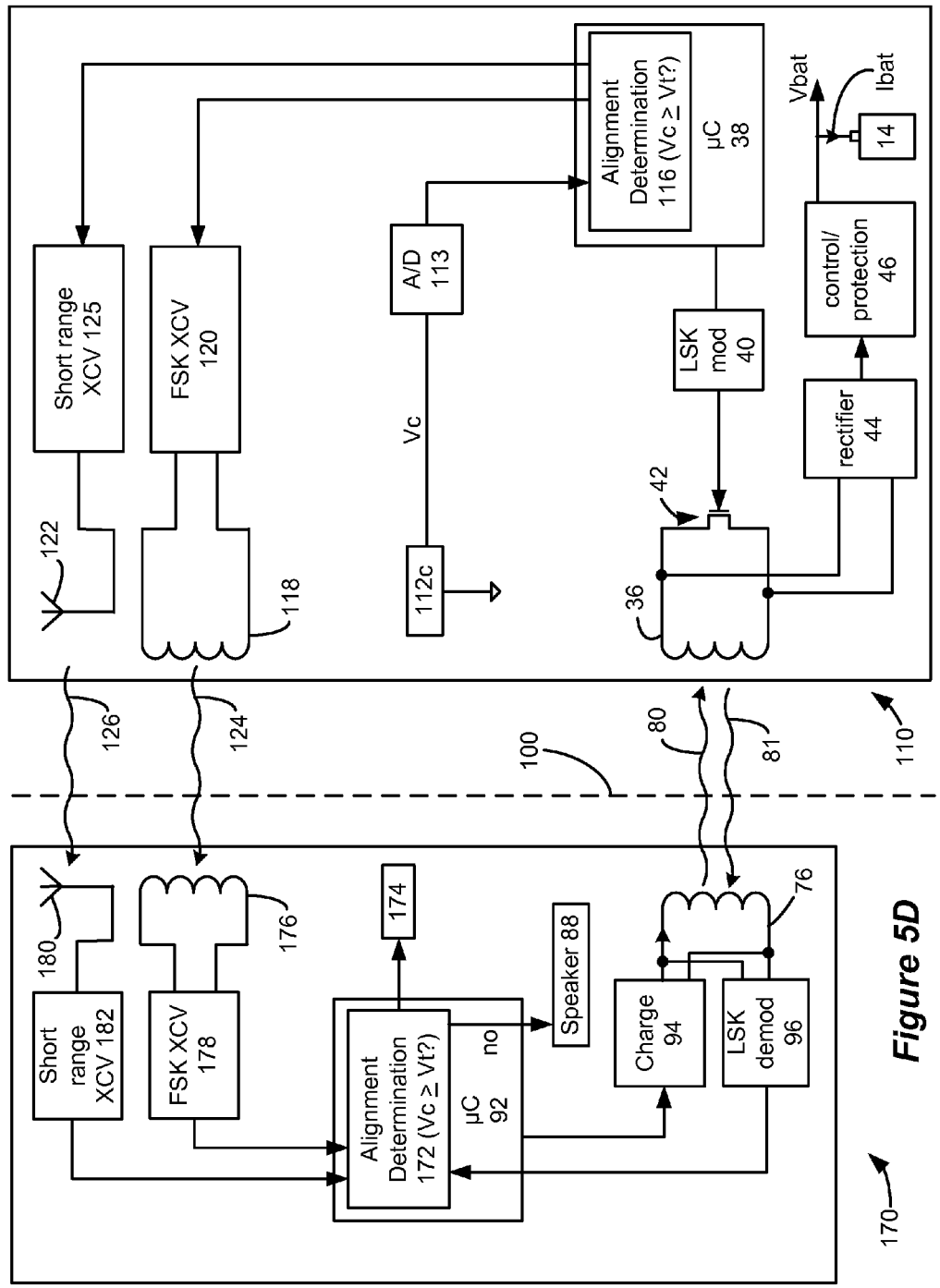
FIG. 5D shows circuitry in the IPG and an improved external charger for determining external charger/IPG alignment using measurements from the at least one magnetic field sensor.

FIG. 5D shows the circuitry in the improved IPG 110 and external charger 170. During a charging session when the external charger 170 is producing a magnetic charging field 80 as described earlier, the magnetic field sensor 112 will sense the strength of this field, and will output (in this example) a voltage, Vc, proportional to the detected field. Such alignment data, e.g., this voltage Vc or an indication derived from it as explained further below, is telemetered to the external charger 170, again as explained further below. (Alignment data comprising or derived from measured field strength data may also include misalignment direction and distance, or indications of these, as explained further below with references to FIGS. 6A-6E).

If values Vc are telemetered to the external charger 170, they can be provided to the external charger's control circuitry 92, which in this case is programmed with an alignment determination module 172 that compares Vc to a threshold, Vt. If Vc is greater than or equal to Vt, the control circuitry 92 will conclude that the magnetic field sensor 112c in the IPG 110 is receiving a suitable amount of the magnetic charging field 80, and hence that the external charger 170 and IPG 110 (i.e., axes 76' and 36') are sufficiently aligned. If Vc is less than Vt, the control circuitry 92 may conclude that alignment is poor and that alignment is not sufficient, and may enable the speaker 88, as described earlier. Based on this alignment information, the user can then attempt to re-position the external charger 170 relative to the IPG 110 until alignment improves and the speaker 88 ceases. Other means of providing alignment information to the user can also be used, such as by enabling one or more lights (LED) 174 on the external charger 170, which is described further below. If a threshold Vt is not used, a single LED 174 can be lit with a brightness that scales with Vc to inform the patient of alignment. Alignment determination module 172 need not be programmed into the control circuitry 92, but could comprise a circuit block discrete from the control circuitry as well.

The alignment data may be telemetered to the external charger 170 at suitable intervals during a charging session. Such intervals need not be periodic, but are preferably frequently enough to allow for alignment determination and user adjustment in essentially real time, such as every second or less. Between such periods of telemetry, the measured values from the magnetic field sensor 112c (e.g., Vc) can be averaged, integrated, or filtered, to smooth out any noise. This can occur at an Analog-to-Digital (A/D) converter block 113, although if the magnetic field sensor 112c includes digitization circuitry, or if the control circuitry 38 in the IPG 110 comprises A/D inputs, use of a discrete A/D block 113 might not be necessary. Analog circuitry can also be used to average, integrate, or filter the measurement (not shown).

The alignment determination steps may be split between the external charger 170 and the IPG 110 in various fashions. In the example just described, magnetic field sensor 112c measurements are averaged, integrated, or filtered at the IPG 100, but then telemetered to the external charger 170 where the alignment determination is made (172). However, the IPG 110 can also contain an alignment determination module 116 to compare the measured values Vc to the threshold Vt. In this case, the IPG 110 makes the alignment determination and need telemeter only a simpler binary alignment indication derived from the measured value to the external charger 170 (e.g., '1' if V≥Vt, or '0' if V<Vt), which then only needs to act on this telemetered data without processing to notify the user of the alignment. Alternatively, values measured by the magnetic field sensor 112c at the IPG 110 may be directly telemetered to the external charger 170 without processing at the IPG 110 (e.g., without averaging, integration, or filtering), leaving these tasks to the external charger 170 as well as the ultimate determination of alignment.

As mentioned earlier, the IPG 110 can telemeter the alignment data to the external charger 170 in any number of manners and using different telemetry circuits. For example, LSK telemetry along link 81 can be used (40, 42) as described in the Background, although this requires a relatively close range. LSK telemetry is preferred if the alignment data to be transmitted is relatively simple (e.g., a binary indication of alignment). Use of LSK telemetry to provide the alignment data requires little changes to the legacy external charger 70 and IPG 10 described in the Background.

Alignment data can also be telemetered to the external charger 170 using telemetry circuitry separate from the links 80 and 81 associated with the magnetic charging field. For example, Frequency Shift Keying (FSK) telemetry can be used along link 124, and as shown in FIG. 5D, the IPG 110 can include FSK transceiver circuitry 120 (e.g., modulation and demodulation circuitry) and an antenna (coil) 118 for this purpose. In legacy IPG systems, components 120 and 118 are typically preexisting in the IPG 110 to facilitate wireless communications with an external controller that is used to adjust the therapy settings of the IPG 110. FSK communications between an external controller and an IPG are disclosed in U.S. Patent Application Ser. No. 61/877,877, filed Sep. 13, 2013, which is incorporated herein by reference, and hence are not further discussed.

Alternatively, alignment data can be telemetered along another short-range telemetry link 126, in which case the IPG 110 could include short-range transceiver circuitry 125 and an antenna 122 compliant with the short-range communications protocol used for the link 126, such as Bluetooth, Bluetooth Low Energy (BLE), Near Field Communication (NFC), Zigbee, or WiFi. Note that if FSK or other short-range protocols are used to transmit alignment data to the external charger 170, the external charger 170 will have corresponding telemetry (receiver) circuitry and hardware (176-182). Although one-way telemetry along links 124 and 126 are needed for the disclosed alignment determination technique, these links could also be bi-directional to allow the external charger 170 to communicate with the IPG 110 for other purposes.

Electromagnetic (EM) telemetry of alignment data along links 124 and 126 may be difficult to employ while the external charger is generating a magnetic charging field 80, because such field is relatively strong and may interfere with the EM telemetry signal. If so, it may be preferable to periodically cease the production of the magnetic charging field 80 during a charging session to allow alignment data telemetry from the IPG 110 to occur. This will increase the duration of the charging session, but not significantly, as such data can be transferred relatively quickly (e.g., on the order of milliseconds) compared to the overall duration of the charging session (e.g., on the order of several minutes or more). Ceasing production of the magnetic charging field 80 during periods of alignment data telemetry is not strictly necessary, particularly if the frequencies used along links 124 or 126 are significantly different from that used for the magnetic charging field 80 (e.g., 80 kHz) and are thus unlikely to cause interference, particularly if band filtering is employed.

In another alternative, alignment data can be transmitted optically to the external charger 170, as described in the above-incorporated '877 application. This telemetry method is beneficial as such optical communications will not interfere with, or be interfered by, the magnetic charging field 80, thus allowing telemetry without periodically ceasing the magnetic charging field 80.

Other useful data relevant to the charging session may also be telemetered from the IPG 110 to the external charger 170 with the alignment data. For example, the IPG's battery voltage (Vbat), the temperature of the IPG (T, as measured by one or more sensors in the IPG; not shown), and/or the battery charging current (Ibat) can be transmitted as well. As explained in the '877 application, these parameters can be used to control the magnetic charging field 80 the external charger 170 produces. For example, if the external charger 170 understands that IPG temperature (T) or the battery charging current Ibat are above thresholds for example, it can reduce the energy of the magnetic charging field 80, by lowering Icharge, or by reducing the duty cycle of the field (i.e., reducing the percentage of the time that the magnetic charging field is being generated). Likewise, the external charger 170 can increase the energy of the magnetic charging field 80 (e.g., increasing Icharge or the duty cycle) if these values for T and Ibat are below such thresholds. Telemetering Vbat with the alignment data may also be used for magnetic charging field 80 control or to monitor the progress of charging generally, as well as to inform the external charger 170 when Vbat has reached a fully-charged threshold so that generation of the magnetic charging field 80 can cease.

The telemetered alignment data can also be used to control the magnetic charging field 80. For example, if the telemetered value for Vc as measured by the magnetic field sensor 112 is below the threshold Vt set by the alignment determination module 172, the control circuitry 92 may increase the energy of the magnetic charging field 80, at least to some safe point consistent with other limitations (e.g., T, Ibat). Conversely, if Vc is significantly above threshold Vt, the control circuitry 92 may reduce the energy of the magnetic charging field 80.

An IPG can be implanted at different depths in different patients, and so an appropriate threshold Vt for the alignment determination module 172 (or 116) may vary from patient to patient. Thus, Vt is preferably established for a given patient during a training phase. For example, when first using the external charger 170, a patient may be instructed to align the external charger 170 and IPG 110 as best she can, and to turn on the external charger 170 to start generating a magnetic charging field 80. The patient may be instructed to then slowly move the external charger 170 relative to the IPG 110 (radially), during which values Vc measured from the magnetic field sensor 112 are telemetered to the external charger 170. The external charger 170 can review these telemetered values for Vc during this training phase, and determine a maximum, which would correspond to a best-case alignment scenario for that patient's IPG 110. The external charger 170 can then set Vt in the module 172 at an appropriate lower value (e.g., 20% of the maximum) to define a region of acceptable (if not perfect) alignment between the external charger 170 and the IPG 110. If module 116 is present in the IPG 110, the IPG 110 can similarly determine and program Vt, and need not telemeter alignment data to the external charger 170 during the training phase.

Figure 1A:
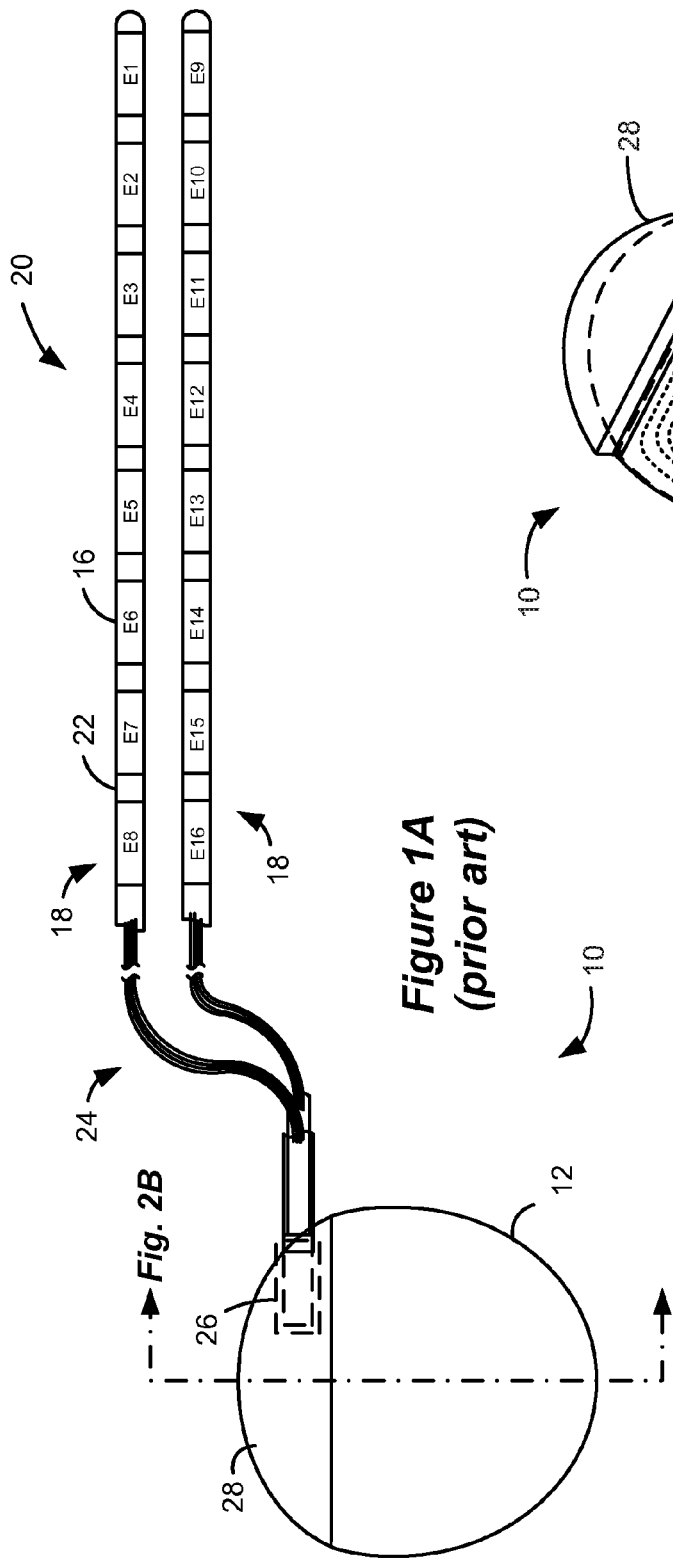
FIGS. 1A and 1B show an Implantable Pulse Generator (IPG) and the manner in which electrodes are affixed in accordance with the prior art.
Figure 1B:
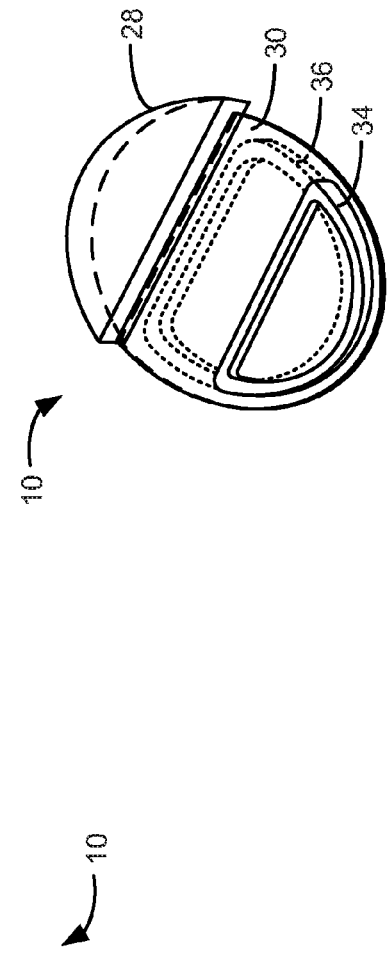
Figure 3:
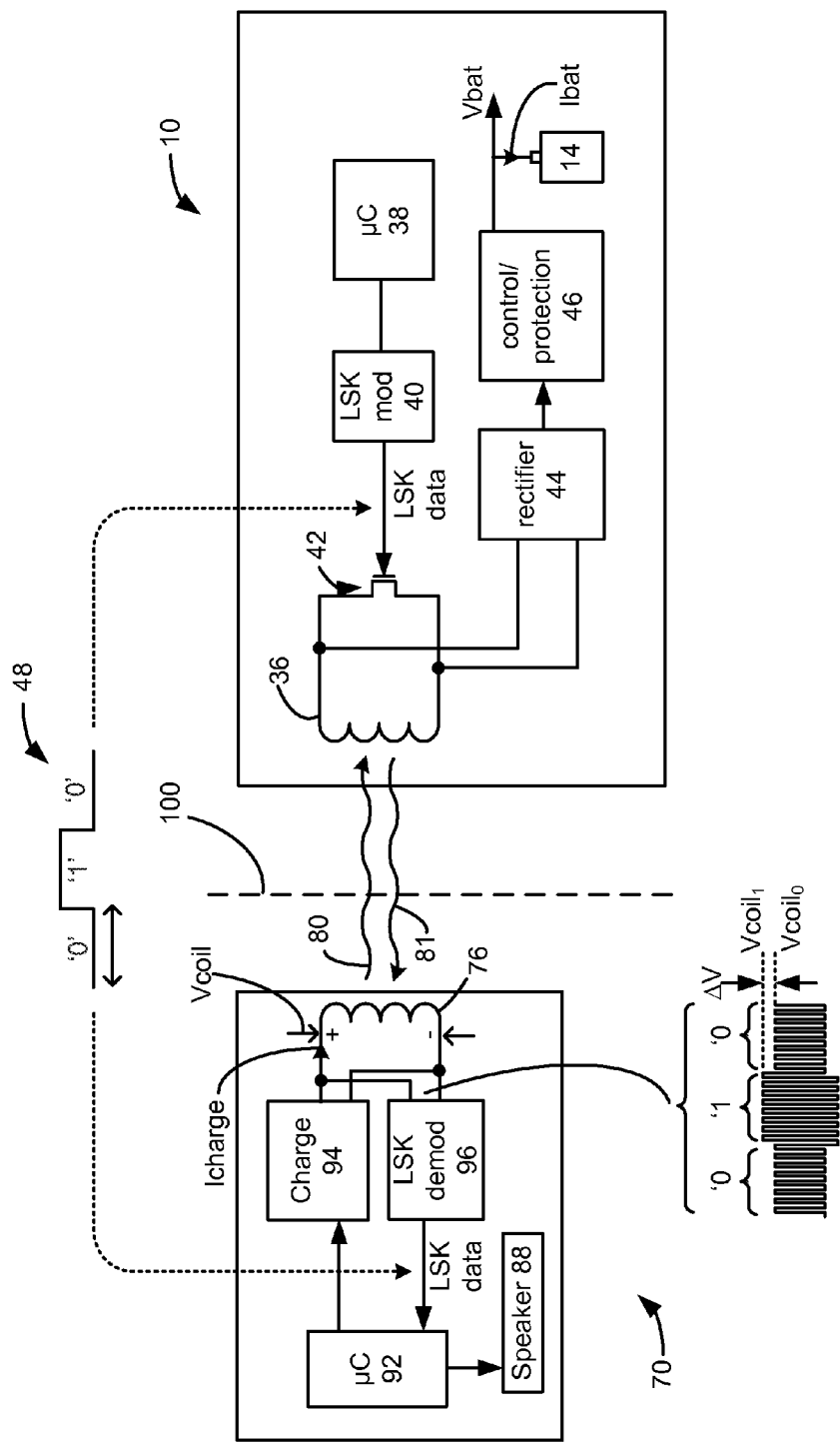
FIG. 3 shows the communication circuitry in the external charger and the IPG in accordance with the prior art.

This disclosed means for determining alignment does not suffer from the same concerns noted earlier with respect to the prior art. By placing the magnetic field sensor 112 in the center of the IPG's charging coil 36, an accurate and direct measurement of the magnetic charging field 80 received by the coil 36 is accomplished, despite any other factors that might attenuate the field, such as the IPG's case 12. Furthermore, because the disclosed technique measures the actually-received magnetic charging field 80 at the IPG 110, it is more accurate that techniques which indirectly determine alignment and coupling by assessing the loading of the charging coil 76 (e.g., Vcoil, FIG. 3) used to produce the magnetic charging field 80. As discussed previously, such techniques cannot reliability discriminate between coupling (loading) resulting from the IPG's coil 36 and coupling (loading) resulting from other conductive structures, such as the case 12.

Figure 6A:
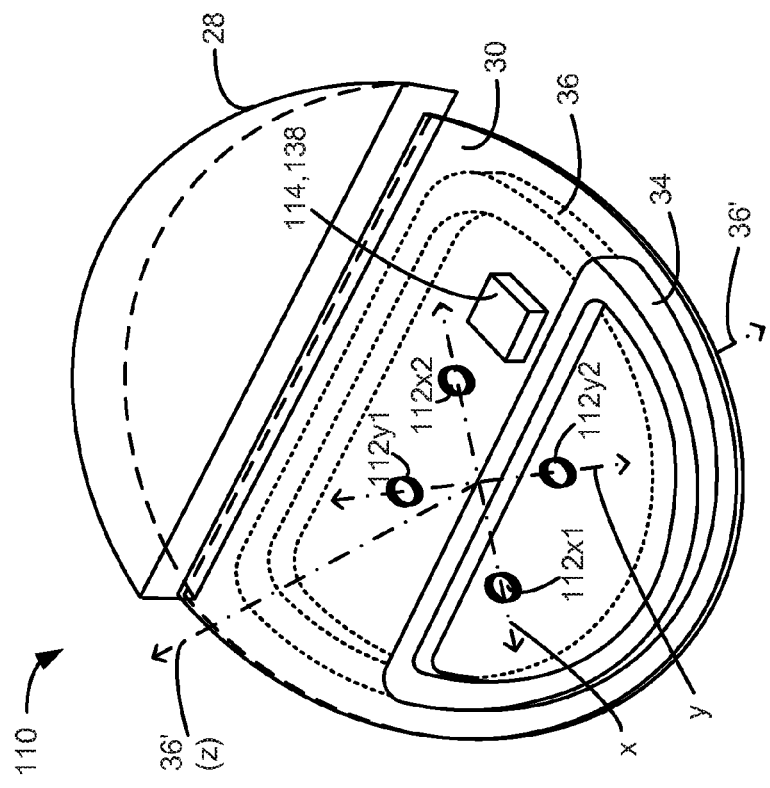
FIGS. 6A and 6B show an improved IPG which includes a plurality of magnetic field sensors.
Figure 6B:
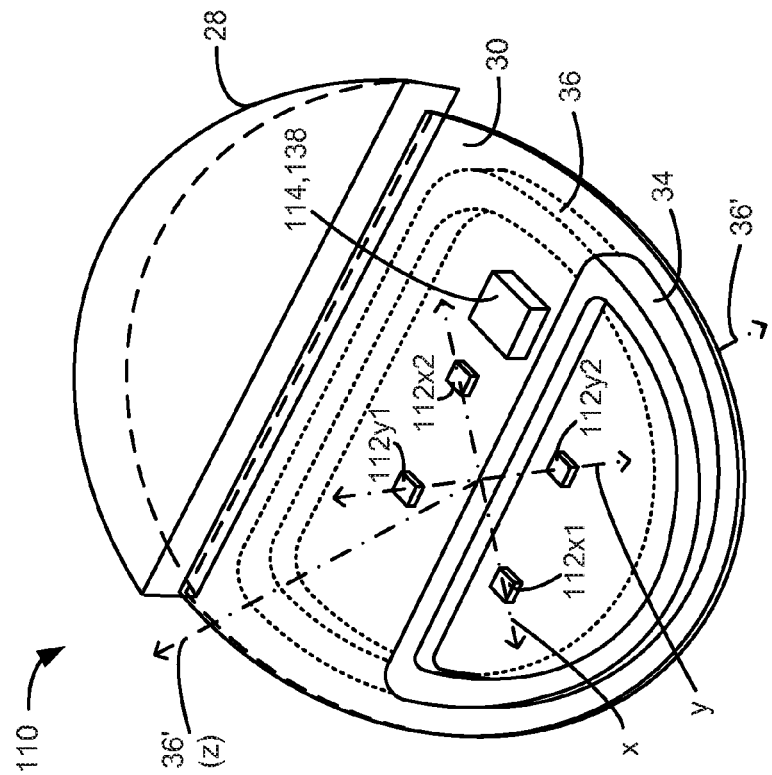

FIGS. 6A-6E illustrate an external charger 170 and an IPG 110 that as well as determining alignment can also determine a direction and/or distance with which the external charger 170 is misaligned with respect to the IPG 110. In FIG. 6A, the PCB 30 of the IPG 110 includes a number of peripheral magnetic field sensors 112 (pick-up coils 112 in FIG. 6B), which are preferably arranged around the center axis 36' at a constant radius. As shown, the sensors 112 occur in pairs: 112$x$1 and 112$x$2 along an x axis, and 112$y$1 and 112$y$2 along a y axis. X and y axes are preferably, but not necessarily, orthogonal to allow misalignment direction and distance to be correlated to an x/y offset of the external charger 170 relative to the IPG 110 without complicated conversions. External charger 170 may have an additional magnetic field sensor 112$c$ at the center axis 36' to allow for alignment determinations as described earlier (FIGS. 5A-5D), but this is not shown in FIGS. 6A-6E for convenience.

Figure 6C:
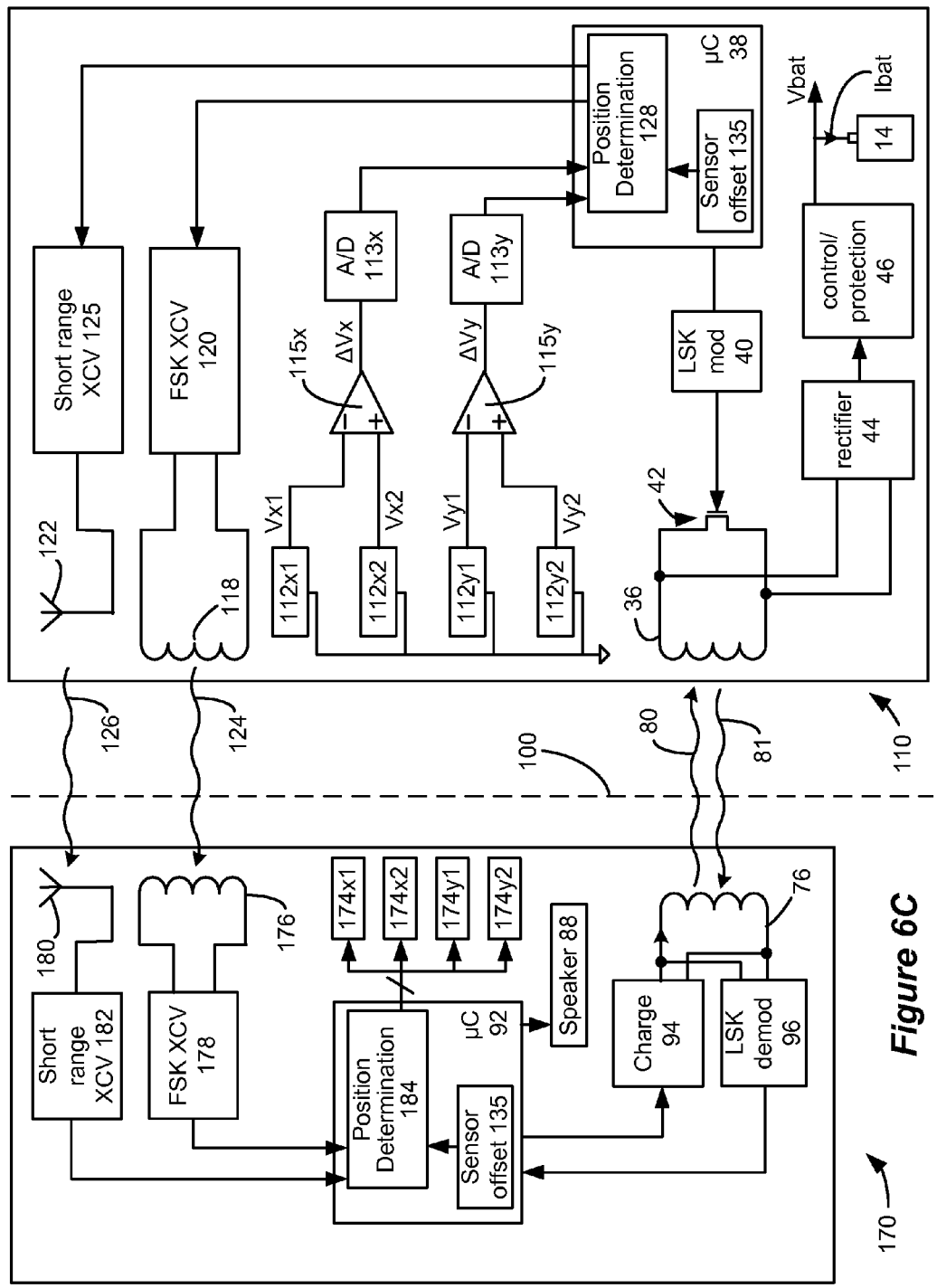
FIG. 6C shows circuitry in the IPG and an improved external charger for determining an external charger/IPG misalignment direction and distance using measurements from the magnetic field sensors.

FIG. 6C shows example circuitry in the devices 170 and 110 used to determine external charger 170/IPG 110 misalignment direction and distance, much of which is similar to the circuitry described earlier, and is thus not repeated. The peripheral magnetic field sensors 112 will receive different strengths of the magnetic charging field 80 depending on external charger/IPG alignment.

Figure 6D:
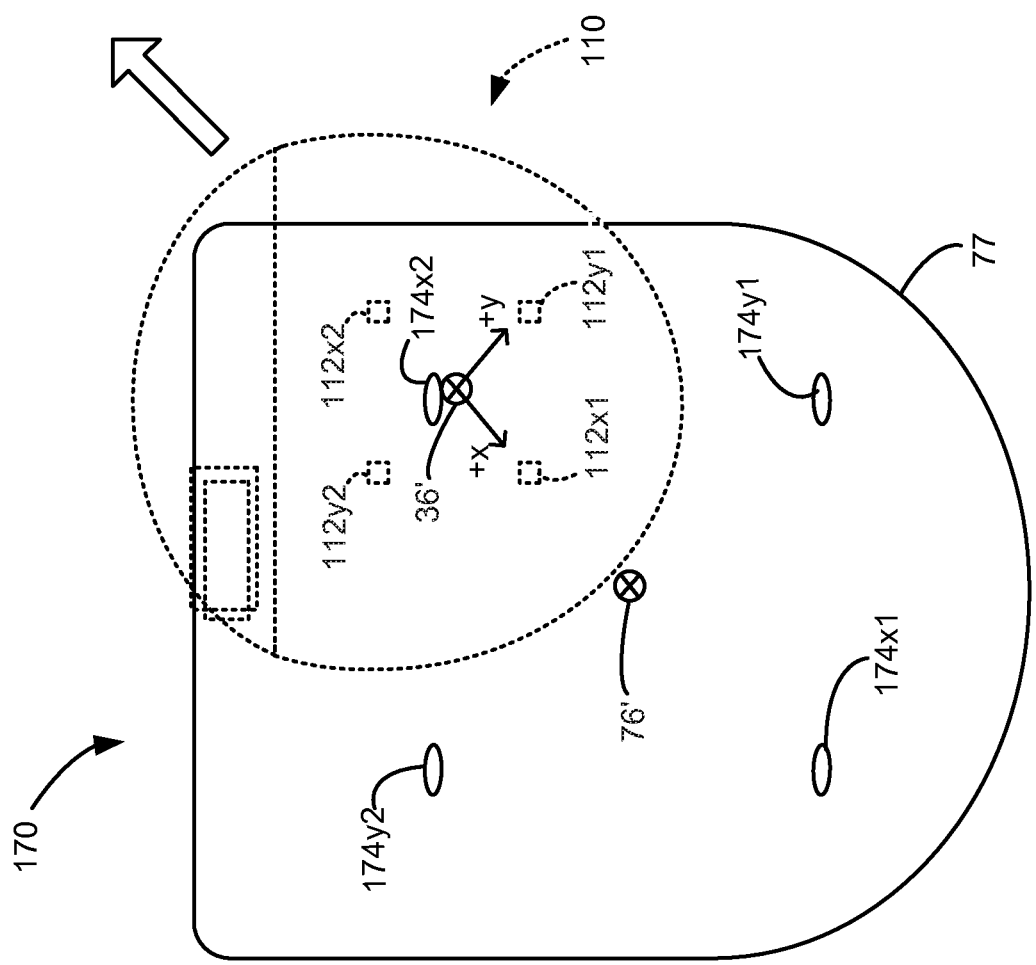
FIG. 6D shows indication of the misalignment direction and distance at a user interface of the external charger.

An IPG 110 underlying an external charger 170 is shown in dotted lines in FIG. 6D to illustrate this. (User interface structures (82; FIG. 2A) from the top of the external charger 170 have been omitted from FIG. 6D for easier viewing). Notice that sensor 112$x$1 is relatively close to the center axis 76' of the external charger's coil 76 and thus Vx1 output from that sensor is relatively high, while sensor 112$x$2 is relatively far and thus Vx2 is relatively low. The difference between these two values ($\Delta$Vx), can be computed by a differential amplifier (diff amp) 115$x$ (FIG. 6C) to determine external charger 170 misalignment, with $\Delta$Vx corresponding to the distance and direction of misalignment in the x axis. In the illustrated example, $\Delta$Vx would be relatively large and negative, denoting that the external charger 170 should be moved a significant distance in the negative x direction. $\Delta$Vy for the y axis can be similarly computed, and diff amp 115$y$ would output a $\Delta$Vy of about zero in the depicted example, as both of sensors 112$y$1 and 112$y$2 are essentially equidistant from the y axis.

These values for $\Delta$Vx and $\Delta$Vy can either be processed at position determination module 128 in the IPG 110 to determine an x/y offset between the external charger 170 and the IPG 110, or these values can be telemetered from the IPG 110 to the external charger 170 and the x/y offset determined at its position determination module 184. Thereafter, the external charger 170 can indicate the misalignment direction and relative distance to the user.

Such misalignment direction/distance information can be provided by the speaker 88 as discussed earlier, but in addition directional indicators 174 are used to visually inform the user in which direction the external charger 170 should be moved to improve alignment and electrical coupling with the IPG 110 during the charging session. These direction indicators 174 in one example can comprise LEDs on the top face of the external charger 170 as shown in FIG. 6D. There may be as many direction indicators 174 as there are magnetic field sensors 112, but this is not strictly necessary as the position determination module 184 can interpolate or extrapolate from different numbers of these devices to indicate the misalignment direction.

Continuing the example of FIG. 6D, upon determining that $\Delta Vx$ or the x offset is large and negative, and that $\Delta Vy$ or the y offset is essentially zero, the position determination module 184 may light LED 174x2 with a strong brightness, LED 174y1 and 174y2 with a moderate brightness, and 174x1 with a low brightness, to inform the patient of the direction that he should move the external charger 170, i.e., in the direction of the brightest LED 174x2, or to the north-east as shown by the arrow in FIG. 6D. The position determination module 184 can control the direction indicators 174 in other manners, such as by pulse rate or color. If alignment data is telemetered frequently enough to the external charger 170, control of the LEDs 174 by the position determination module 184 can occur in essentially real time to allow a patient to visually assess their progress toward achieving better alignment as she moves the external charger 170 by viewing the LEDs.

Once aligned, the LEDs 174 may be lit with a uniform moderate brightness indicating a balanced (aligned) condition, at which time alignment information from the speaker 88 might also cease. Enablement or disablement of the speaker 88 though need not coincide with enablement or disablement of the LEDs 174, and instead use of the speaker 88 may be limited to gross misalignment conditions, for example, when no magnetic field sensor 112 in the IPG 110 is receiving a sufficient strength of the magnetic charging field 80. Speaker 88 may also be dispensed with. Additionally, the disclosed alignment techniques may also be used in conjunction with the prior art alignment techniques described earlier, for example, by using prior art techniques for coarse alignment assessment and adjustment, with the disclosed techniques then used for fine alignment assessment and adjustment.

Many modifications can be made. For example, diff amps 115x and 115y may not be necessary, and instead the values for Vx1, Vx2, Vy1, and Vy2, or indications of them (e.g., based on thresholds Vt used for each, which may be different), or data derived from them, could be telemetered to the external charger 170 for processing and comparison at the position determination module 184. Diff amps can also be provided to measure the differences in received field strength between adjacent magnetic field sensors around the center axis 36', e.g., between sensors 112y1 and 112x2; 112x2 and 112y2; etc. Differential measurements between the sensors and an additional magnetic field sensor at the center axis 36' (112c; not shown) may also be used. Aspects of the position determination module 184 can also be included in the IPG 110 (128), which processing can reduce the amount of data that needs to be telemetered to the external charger 170. For example, the IPG 110 may simply telemeter a misalignment direction and information concerning the relative misalignment distance as computed in module 128, which the external charger 170 present as alignment information to the user. Different numbers of magnetic field sensors 112 could be used. For example, alignment data from three sensors 112 can be used by module 184 (or 128) to triangulate $\Delta Vx$ and $\Delta Vx$ and the x/y offset.

While it is desired that the peripheral magnetic field sensors 112 be equidistant from the center axis 36' of the IPG's charging coil 36 to simply misalignment direction and distance determinations, this is not strictly required. To assist with determining misalignment direction and distance in the case where the sensors 112 are not equidistant, and as shown in FIG. 6C position determination module 184 (or 128) can be programmed with sensor offset data 135. As well as assisting with determining misalignment direction, such data 135 can be used to determine a precise determination of misalignment distance, instead of a relative distance as described to this point.

Figure 6E:
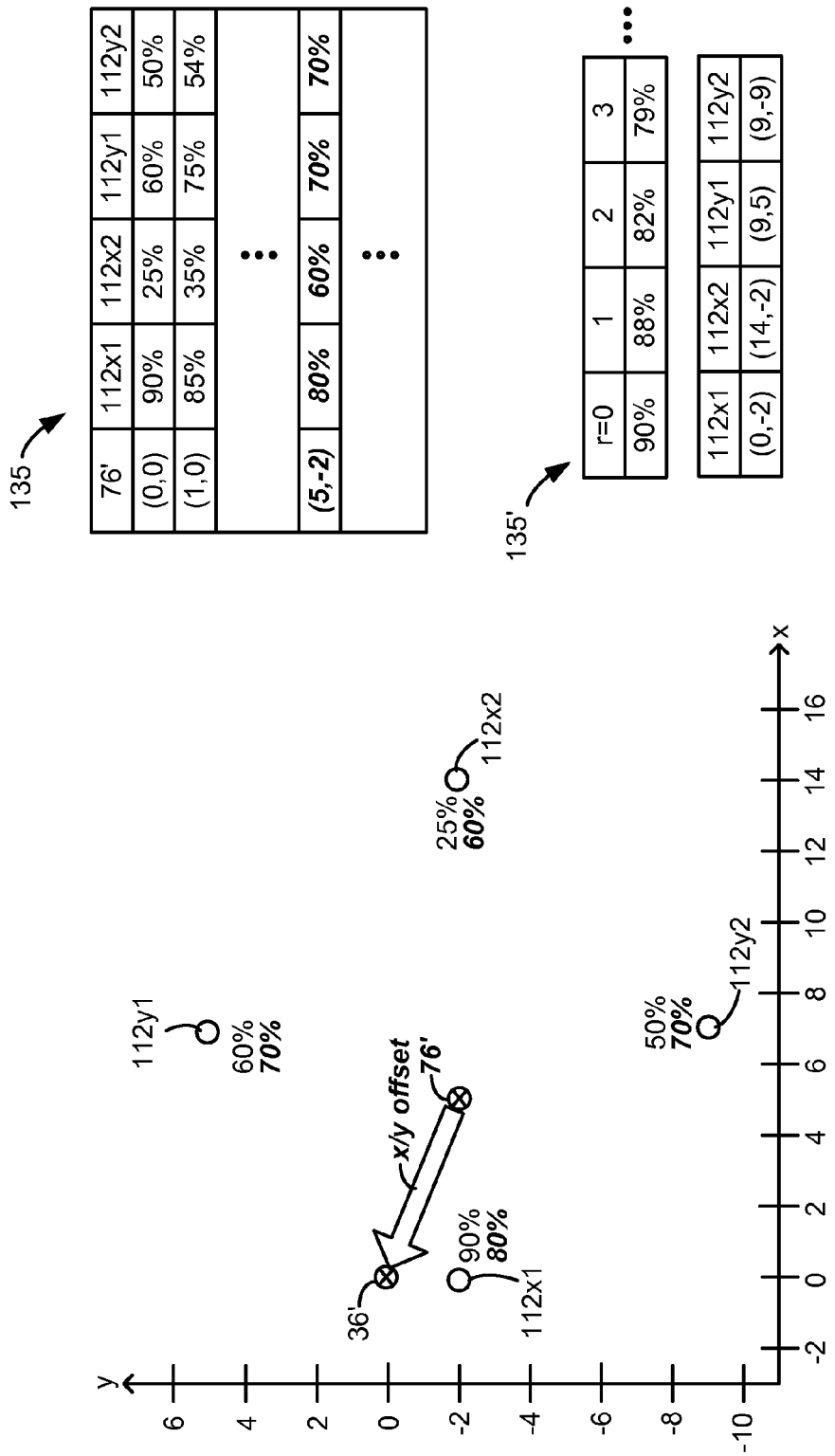
FIG. 6E shows use of sensor offset data to determine misalignment direction and distance.

FIG. 6E shows the magnetic field sensors 112 at random (x,y) coordinates on the IPG's PCB 30 (in millimeters), with the center axis 36' being represented as coordinate (0,0). Further shown is sensor offset data 135 for each of the sensors 112. In the depicted example, sensor data 135 includes a percentage of the maximum field strength that each sensor 112 would expect to measure were the external charger 170 in ideal alignment with the IPG 110, i.e., if axes 76' and 36' were collinear and not radially offset (0,0). Thus, at this no-offset condition, sensor 112x1, which is relatively close, would expect to see a relatively high percentage of the maximum field (90%), while sensor 112x2, which is relatively far would expect a low percentage (e.g., 25%). Sensors 112y1 and 112y2 are in between the other sensors, and would expect to see 60% and 50% respectively. Sensor offset data 135 can also include strengths sensors 112 would expect to measure if the external charger 170 was misaligned with respect to the implantable medical device at different x/y offsets (x,y). The strengths (percentages) in sensor offset data 135 can be determined by testing, or by knowing the radial intensity of the magnetic charging field at a given depth, d.

Suppose that the external charger 170 (axis 76') is misaligned as shown in FIG. 6E. In this instance, sensor 112x1 is still closest to axis 76' and would thus measure the highest percentage (80%), although smaller than the percentage received when alignment is ideal (90%). Sensor 112x2 is still farthest away from axis 76', but much less so, and so receives a higher percentage (60%) compared to its ideal value (25%). Sensors 112y1 and 112y2 are equally moderately distant from axis 76', and both measure a percentage of 70%.

From these measurements, the external charger 170 or IPG 110 can consult sensor offset data 135 to find percentages that match the measurements, and thus to derive the alignment data using both the measured strengths and the sensor offset data. In this instance, the measured percentages best correspond to a location of the center axis 76' at coordinate (5,−2) in the sensor offset data 135, thus providing an x/y offset from which both misalignment direction and a precise measurement for the misalignment distance can be determined, as represented by the arrow. Once the x/y offset, or the already-determined direction and distance, are telemetered to the external charger 170, the direction and distance can be indicated to the user to improve alignment, i.e., by instructing the user to move the external charger 170—5 millimeters in the x direction, and 2 millimeters in the y direction. Again, LEDs 174 can enabled proportionally to these determined direction and distance parameters.

Sensor offset data could be represented and used to determine a misalignment direction and distance in other ways as well. For example, sensor offset data 135' in FIG. 6E includes field strength as a function of radius at the particular IPG depth, and the coordinates of the sensors 112. From the measured percentages at each of the sensors 112, a location of the center axis 76' relative to the sensors 112 can be determined using the percentages, with the coordinates of the sensors 112 then used to determine a fixed coordinate of the center axis 76,' i.e., the x/y offset. Sensor offset data could also comprise thresholds (see, e.g., FIG. 5D) for each of the sensors 112 which vary depending on sensor distance from the center axis 36'.

While sensor offset data 135 is particularly useful in situations in which the sensors 112 are not equidistant from the center axis 36' of the IPG 110, it can also be useful when used with equidistant sensors 112 (e.g., FIGS. 6A and 6B) to more precisely determine misalignment distance, as just described. Sensor offset data 135 can be stored in any memory in the IPG 110, or can be stored in an ASIC 114, as described further below with reference to FIGS. 8A and 8B.

A training phase can also assist with determining the sensor offset data 135, for example, by allowing realistic percentages in the sensor offset data 135 to be determined or scaled as necessary.

While beneficial to compute both a misalignment direction and a misalignment distance, some charging applications may only require one or the other, most likely misalignment direction. It should also be noted that while a misalignment direction determination requires the use of more than one sensor 112, a misalignment distance determination can occur using only one sensor. For example, and referring to the sensor offset data 135' in FIG. 6E, if a single sensor (say 112x2) is receiving a field strength of 82%, it can determine that it is r=2 millimeters from axis 76', and because sensor 112x2 is (14, −2) away from the center axis 36,' the misalignment distance between the axes 36' and 76' can be determined, although not the direction, given the radial symmetry of the magnetic field. Note that this allows alignment sufficiency to be determined even if a single sensor is not located at the center axis 36' of the IPG's charging coil 36. For example, the determined distance (e.g., 2 mm) can be compared to a distance threshold (e.g., 5 mm) to determine whether alignment is sufficient or not and to inform the patient accordingly, as described earlier with respect to FIG. 5A-5D.

Figure 7:
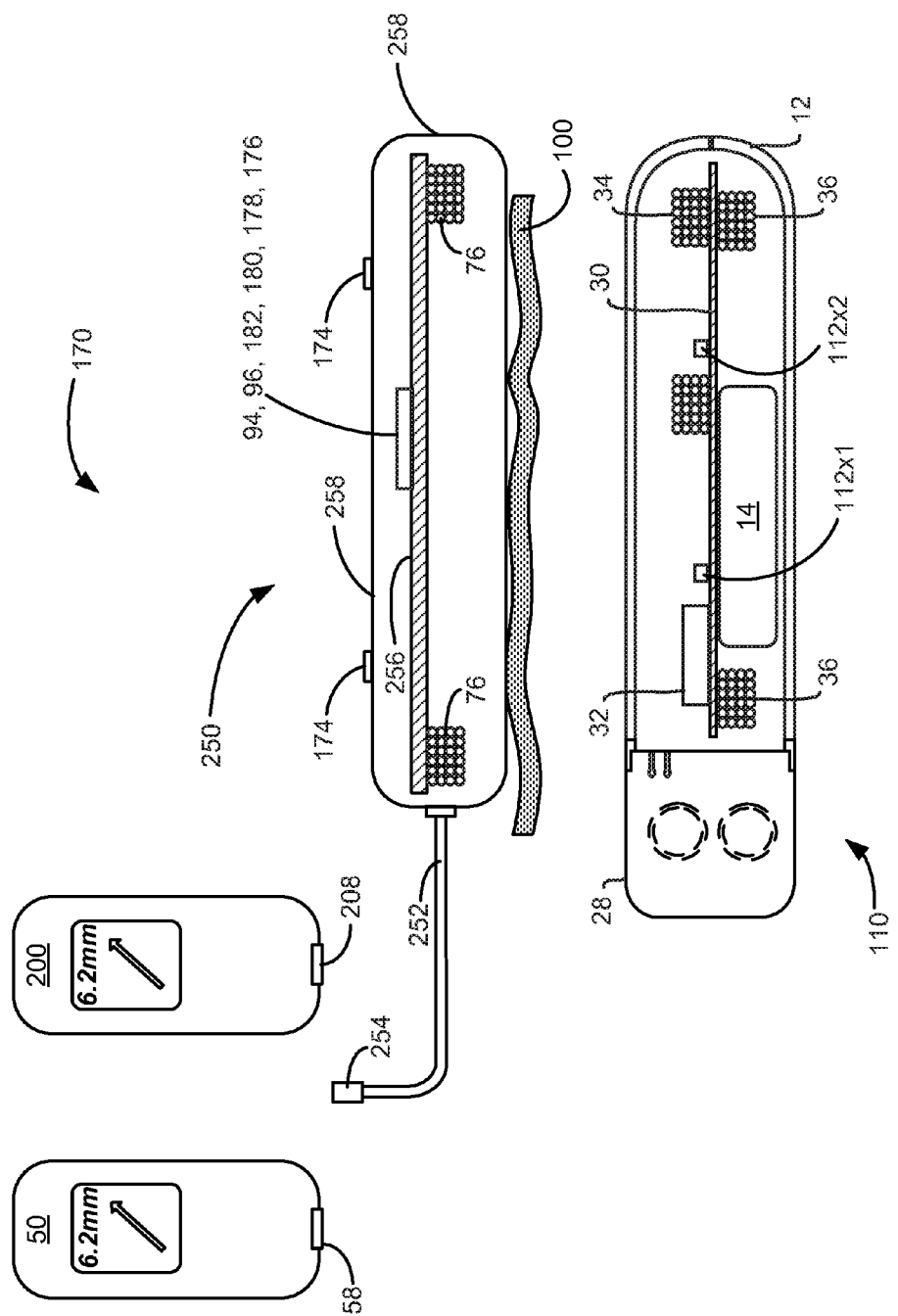
FIG. 7 shows an improved external charger for use with the improved IPG which includes a charging head coupled to a mobile controller.

FIG. 7 shows another embodiment of an external charger 170 that can benefit from use of the disclosed alignment detection techniques. In this example, charging coil 76 has been moved into a charging head 250 with a housing 258. The charging head 250 includes a PCB 256 which may contain many of the previously-mentioned circuit components in the external charger (for example, antennas 180 and 176, transceivers 182 and 178, charging circuitry 94, and LSK demodulator 96).

The charging head 250 is coupled to a mobile controller with a graphical user interface, such as a dedicated external controller of the type used in legacy IPG systems, or a multi-functional mobile device 200 such as a cell phone, a tablet computer, or another hand-holdable portable control device. See the above-incorporated '877 application for further details concerning such mobile controllers. As depicted, the charging head 250 includes a cable 252 and a connector 254 that can couple to appropriate ports 58 or 208 on the relevant mobile device, whose graphical user interface can allow the user to start a charging session and to receive and review alignment. Power for the charging head 250, as well as to generate the magnetic charging field 80 from the charging coil 76, can come from the mobile controller via cable 252.

The external charger 170 can otherwise operate as described earlier to determine charging head 250/IPG 110 alignment. Such alignment information may be presented to the patient using one or more LEDs 174 on the head's housing 258 as described earlier. Or, the graphical user interface of the mobile controller can be used to display or audibly announce the alignment data. For example, the display of the mobile controller in FIG. 7 informs as to both a misalignment direction (the arrow), and a misalignment distance (6.2 mm), computed as described earlier with reference to FIGS. 6A-6E. The graphical user interface may also be used to inform whether alignment is sufficient or not, as described earlier with references to FIGS. 5A-5D.

The external charger 170, while having different pieces, may be more convenient for a patient because it allows the charging head 250 to be placed proximate to the IPG 110 (such as in a belt with a pocket, or adhered to the patient's tissue 100 using double sided tape), while the mobile controller remains relatively distant from the IPG 110 by virtue of the length of cable 252. This makes IPG charging easier, particularly if the IPG 110 is located in an area behind the patient, as occurs in an SCS application, as it permits the graphical user interface of the mobile controller to be held and seen in front of the patient.

Figure 8A:
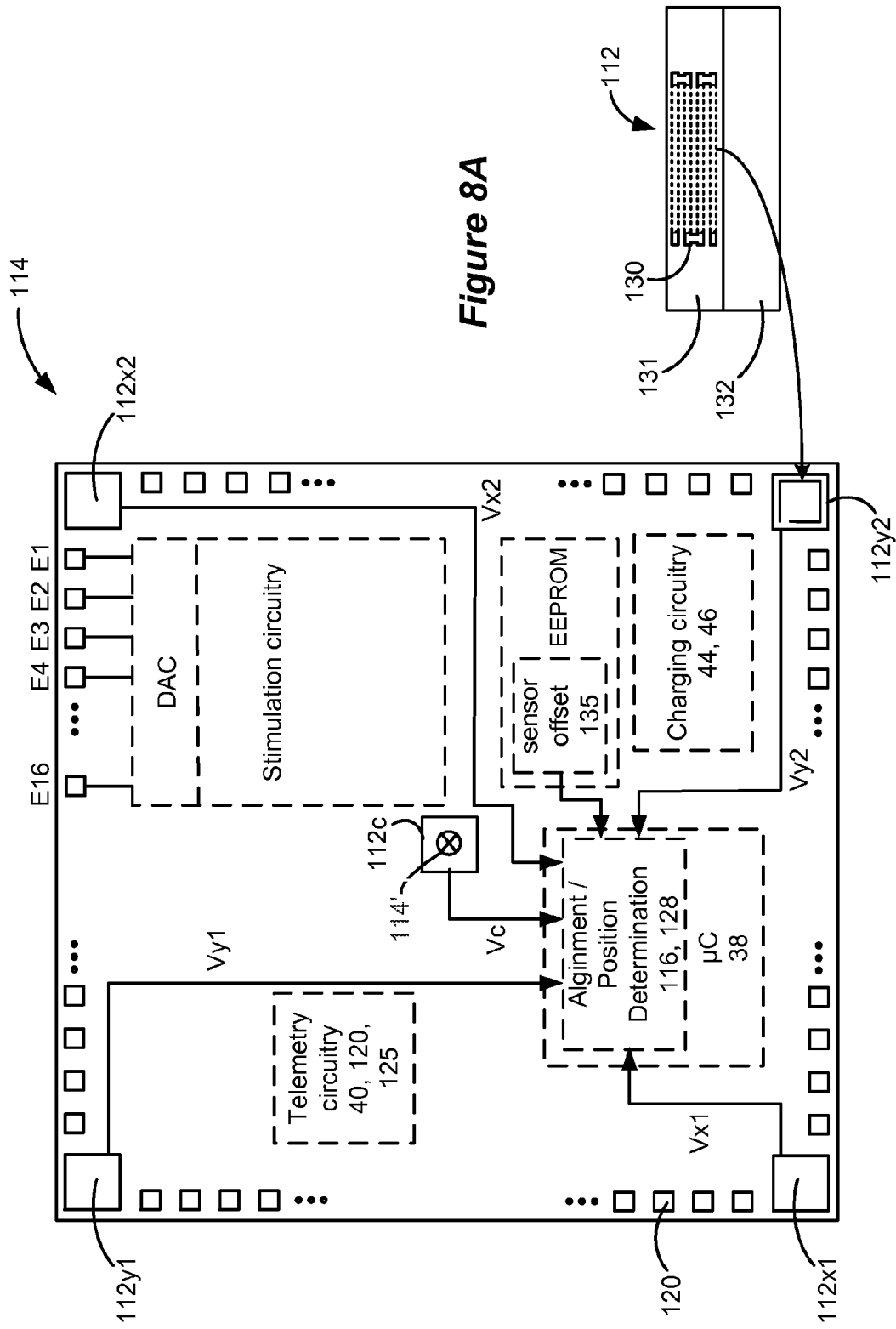

FIGS. 8A-9B show alternative locations for the one or more magnetic field sensors 112 in the IPG 110. In FIG. 8A the one or more sensors 112 are integrated with an integrated circuit used in the IPG 110, while in FIG. 8B the one or more sensors 112 are integrated with the integrated circuit's package. In the example shown, the integrated circuit comprises an Application Specific Integrated Circuit (ASIC) 114 of the type disclosed in U.S. Patent Application Publications 2013/0023943 and 2012/0095529, which are both incorporated herein by reference.

ASIC 114 is typically built on a semiconductive substrate 132 and includes several functional blocks for the IPG 110, some of which have already been described. For example, ASIC 114 can include telemetry circuitry (e.g., 40, 120 and/or 125) that couple off chip to the IPG charging coil 36, telemetry coil 118, and/or short-range antenna 112 (FIG. 5D). A stimulation circuit block is coupled to the electrodes E1-E16 and includes Digital-to-Analog Converters (DAC) responsive to a stimulation program (which dictates which electrodes are active to provide pulses, as well as pulse magnitude, polarity, frequency, and width) to generate the therapeutic current pulses appearing at those electrodes. An EPROM block caches any relevant data in the system (such as log data), and may contain the sensor offset data 135 described earlier (even if the sensors are outside of the ASIC 114). Charging circuitry (e.g., 44 and 46) is coupled to the charging coil 36 and battery 14 (if present) off chip. ASIC 114 can also include the IPG's main control circuitry 38, which as noted earlier can be programmed with either or both of the alignment 116 or position 128 determination modules (FIGS. 5D, 6C). The various blocks communicate on the ASIC 114 via an address/data bus (not shown). ASIC 114 contains several terminals 120 (e.g., bond pads, solder bumps, etc.) necessary to connect the ASIC 114 to pins in its package and ultimately to other circuitry and components in the IPG 110.

In FIG. 8A, peripheral magnetic field sensors 112 appear at the corners of the ASIC 114, although such positioning is not strictly necessary. A center magnetic field sensor 112c appearing at the center axis 114' of the ASIC 114 can also be provided as shown. Values of the magnetic charging field 80 measured at the sensors (Vx1, Vx2, Vy1, Vy2, Vc) are reported to the control circuitry 38, and to modules 116 or 128 if present, and are ultimately telemetered to the external charger 170 as alignment data.

The ASIC's center axis 114' is preferably located on the IPG's PCB 30 at the center axis 36' of the IPG's charging coil 36. If the ASIC 114 is so located, magnetic field sensor 112c will be located at the center axis 36,' and therefore the alignment determination can occur as set forth in FIGS. 5A-5D. Because peripheral magnetic field sensors 112x1, 112x2, 112y1, and 112y2 would be equidistant to center axis 36', and misalignment direction and distance determinations can occur as set forth in FIGS. 6A-6D.

However, centrally locating the ASIC 114 on the PCB 30 may not always be possible. For example, as shown in FIG. 5A, the ASIC 114 is displaced from the center axis 36' (134) in x and y directions as measured from the center axis 114'. If so, sensor offset data 135 can be programmed into the ASIC 114 to allow misalignment direction and distance determinations to be made as discussed earlier with reference to FIG. 6E. Sensor offset data 135 can also be used if the sensors 112 are not equidistant from axis 36' for some other reason, such if they appear in random locations on the ASIC 114.

Magnetic field sensors 112 such as Hall effect or GMR sensors can be fabricated using CMOS processes typically used to form the ASIC 114. See, e.g., M. Paun, "Hall Effect Sensors Design, Integration and Behavior Analysis," J. Sensor & Actuator Networks, Vol. 2, at 85 (February 2013); C. Reig, "Magnetic Field Sensors Based on Giant Magnetoresistance (GMR) Technology: Applications in Electrical Current Sensing," Sensors, Vol. 9, at 7919 (October 2009). Alternatively, and as shown in the cross section of FIG. 8A, the sensors 112 may be formed as coils in the conductive layers of the ASIC 114. For example, coils can be formed in the different metal layers 130 typically present in the ASIC 114 (four such layers are shown in the cross section), with coils at each layer connected by one or more vias to lengthen the coil and improve its detection sensitivity. One or more dielectric layers 131 can isolate the coil sensor 112 fabricated in this fashion.

FIG. 8B shows one or more magnetic field sensors 112 integrated with the package 138 of the ASIC 114. For example, peripheral sensors 112$x$1, 112$x$2, 112$y$1, and 112$y$2 appear at the corners of the package 138, and may reside on the package's lead frame 136 if the package 138 is mold injected, or within a cavity 136 if the package 138 is ceramic. Pins 140 or similar structures such as ball grid arrays allow the package 138 to be solder mounted to the IPG's PCB 30 in a traditional fashion. The peripheral sensors 112$x$1, 112$x$2, 112$y$1, and 112$y$2 can be wire bonded to the ASIC 114 via bond pads 120, or via conductive traces within the package 138 if it is a multi-chip package. Again, the package 38 is preferably mounted at center axis 36' for the reasons noted earlier, but could be mounted elsewhere while still providing necessary alignment data to the external charger 170, perhaps in conjunction with sensor offset data 135. Although not shown, additional sensors 112 could also be included on top or the bottom of the ASIC 114 in a vertical stacking configuration. Again, one or more sensors 112 so integrated with the ASIC's package 138 can be used to telemeter alignment data to the external charger 170 in the various ways previously described.

Although disclosed as integrated with the main ASIC 114 that provides the bulk of the electrical functionality in the IPG 110, the magnetic field sensors 112 could be integrated with other integrated circuits in the IPG 110 as well. Or, an integrated circuit with only the magnetic field sensors 112 could be separately provided.

Figure 9A:
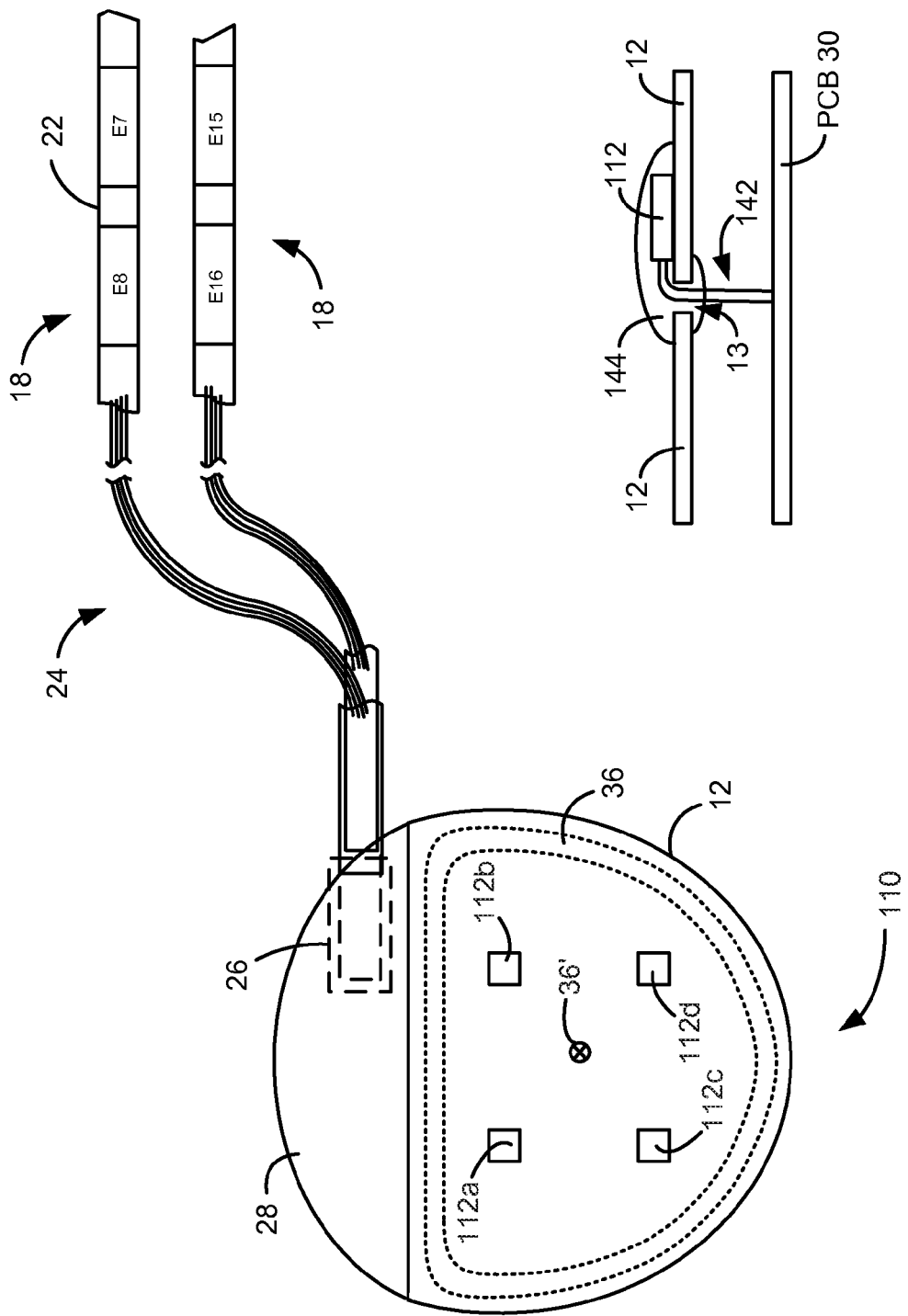
FIGS. 9A and 9B show incorporation of the one or more magnetic field sensors outside or inside of the case of the improved IPG.
Figure 9B:
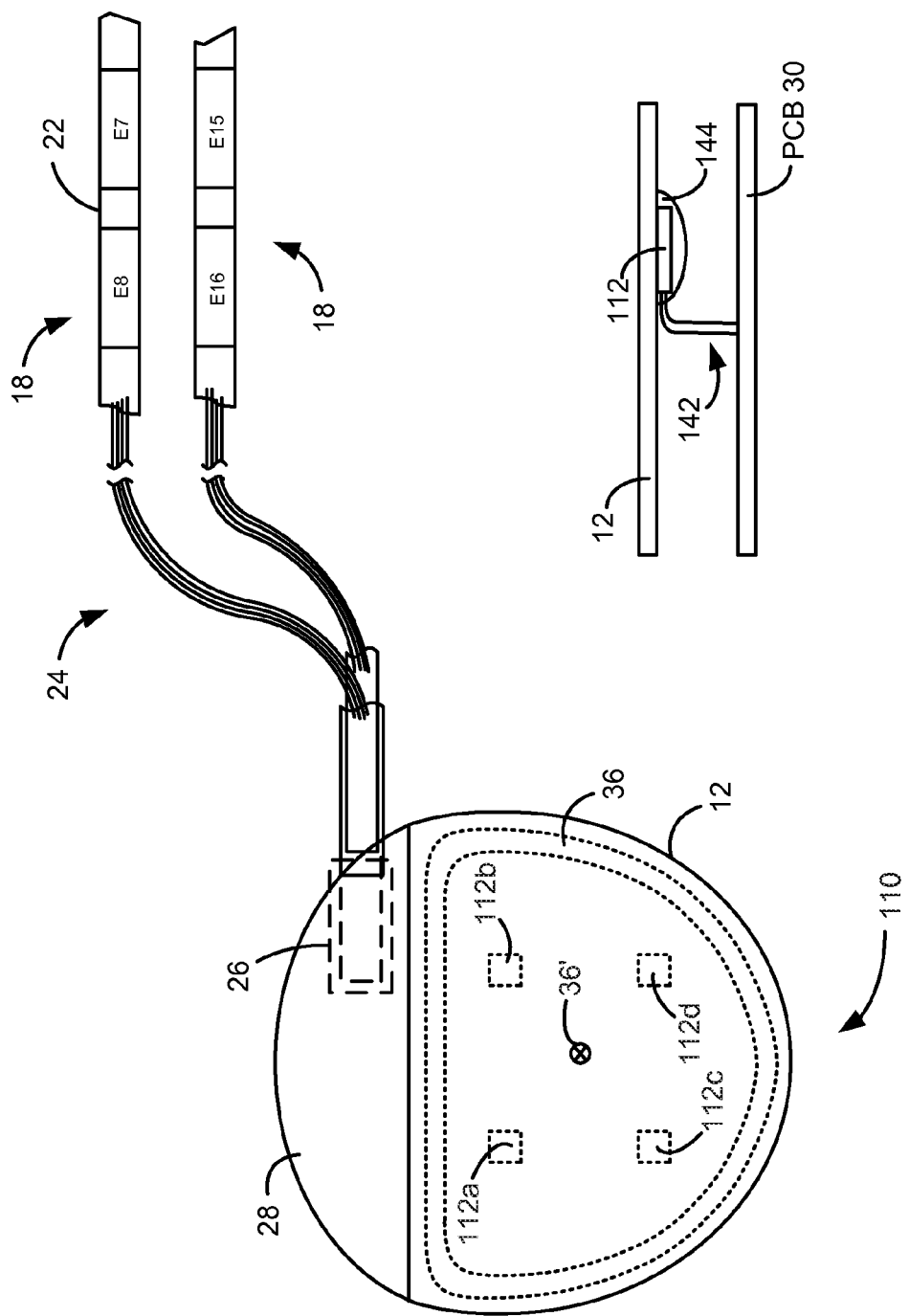

FIGS. 9A and 9B show one or more sensors 112 alternatively located with respect to the IPG's case 12. In FIG. 9A, the sensors 112 are affixed to the outside of the case 12, and are coupled via lead wires 142 to the PCB 30 through a hole 13 in the case, as shown in cross section. After being electrically connected, the hole 13 and the sensors 112 can be hermetically sealed with epoxy 144 for example. In FIG. 9B, the sensors 112 are affixed to the inside of the case 12, and so case holes 13 aren't required. Sensors 112 are again preferably located at or equidistant from the center axis 36', but this is not required for the reasons previously described. Again, one or more sensors 112 so affixed to the IPG's case 12 can be used to telemeter alignment data to the external charger 170.

Although the external charger 170 has largely been disclosed as a means for charging the IPG's battery 14 (FIG. 2B), it should be understood that the external charger 170 and the disclosed alignment determination techniques can be used to provide a magnetic charging field 80 to an IPG 110 that has no battery, i.e., in an application in which the external charger 170 constantly provides operational power for the IPG 110. Alignment of the external charger 170 and the IPG 110 is still critical in such an application, whether or not the received operational power is ultimately used to charge a battery.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. An implantable medical device, comprising:
   a coil configured to receive a magnetic charging field from an external charger, wherein the coil comprises a center axis;
   a plurality of magnetic field sensors each configured to measure a strength of the magnetic charging field, wherein one of the plurality of magnetic field sensors is located at the center axis of the coil and wherein others of the plurality of the magnetic field sensors are located equidistant to the center axis;
   telemetry circuitry configured to transmit alignment data to the external charger, wherein the alignment data is indicative of external charger alignment with respect to the implantable medical device, and wherein the alignment data comprises or is derived from the measured strengths; and
   charging circuitry configured to use the received magnetic charging field to provide operational power to the implantable medical device.

2. The device of claim 1, wherein the magnetic field sensors are oriented to measure the strength of the magnetic charging field in a direction parallel to an axis of the coil.

3. The device of claim 1, wherein the magnetic field sensors comprise a coil.

4. The device of claim 1, wherein the magnetic field sensors comprise Hall sensors or giant magnetoresistance sensors.

5. The device of claim 1, further comprising a circuit board, wherein the magnetic field sensors are affixed to the circuit board.

6. The device of claim 1, further comprising an integrated circuit, wherein the magnetic field sensors are integrated with the integrated circuit or a package of the integrated circuit.

7. The device of claim 6, wherein the integrated circuit comprises the telemetry circuitry and the charging circuitry.

8. The device of claim 6, wherein the integrated circuit comprises stimulation circuitry configured to generate therapeutic currents at at least one electrode of the implantable medical device.

9. The device of claim 1, further comprising a case for housing the coil, the telemetry circuitry, and the charging circuitry.

10. The device of claim 9, wherein the magnetic field sensors are affixed to an inside or outside of the case.

11. The device of claim 1, further comprising a rechargeable battery, wherein the charging circuitry is configured to use the received magnetic charging field to provide operational power to the implantable medical device by charging the battery.

12. The device of claim 1, wherein the alignment data comprises an indication whether or not the external charger is sufficiently aligned with the implantable medical device.

13. The device of claim 1, wherein the alignment data comprises a comparison of the measured strengths to at least one threshold.

14. The device of claim 1, wherein the alignment data comprises a direction with which the external charger is misaligned with respect to the implantable medical device, or a distance with which the external charger is misaligned with respect to the implantable medical device, or both.

15. The device of claim 1, wherein the alignment data comprises an x/y offset with which the external charger is misaligned with respect to the implantable medical device.

16. The device of claim 1, wherein the telemetry circuitry is configured to transmit the alignment data to the external charger by modulating an impedance of the coil during receipt of the magnetic charging field.

17. The device of claim 1, wherein the telemetry circuitry is configured to transmit the alignment data to the external charger via a link separate from the magnetic charging field.

18. The device of claim 1, further comprising a battery, wherein the telemetry circuitry is further configured to transmit to the external charger one or more of a temperature of the implantable medical device, a charging current for the battery, or a voltage of the battery.

19. The device of claim 1, further comprising a memory comprising sensor offset data indicative of a location of each of the one or more plurality of magnetic field sensors in or on the implantable medical device.

20. The device of claim 19, further comprising control circuitry configured to derive the alignment data from the measured strengths and the sensor offset data.

21. The device of claim 19, wherein the at least one location is relative to a center axis of the coil.

22. The device of claim 19, wherein the sensor offset data comprises a strength each of the magnetic field sensors would expect to measure if the external charger was ideally aligned with the implantable medical device.

23. The device of claim 19, wherein the sensor offset data comprises a strength each of the magnetic field sensors would expect to measure if the external charger was misaligned with respect to the implantable medical device at a plurality of x/y offsets.

24. The device of claim 19, wherein the sensor offset data comprises data indicating a strength of the magnetic charging field as a function of radius.

* * * * *